(12) United States Patent
Francischelli et al.

(10) Patent No.: US 7,706,882 B2
(45) Date of Patent: Apr. 27, 2010

(54) METHODS OF USING HIGH INTENSITY FOCUSED ULTRASOUND TO FORM AN ABLATED TISSUE AREA

(75) Inventors: David E. Francischelli, Brooklyn Park, MN (US); James B. Hissong, Jacksonville, FL (US); James R. Keogh, Brooklyn Park, MN (US); James R. Skarda, Lake Elmo, MN (US); Mark T. Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 1310 days.

(21) Appl. No.: 11/128,686

(22) Filed: May 13, 2005

(65) Prior Publication Data

US 2006/0025756 A1 Feb. 2, 2006

Related U.S. Application Data

(63) Continuation-in-part of application No. 10/464,213, filed on Jun. 18, 2003, now Pat. No. 6,936,046, which is a continuation of application No. 09/629,194, filed on Jul. 31, 2000, now Pat. No. 6,595,934, which is a continuation-in-part of application No. 09/487,705, filed on Jan. 19, 2000, now abandoned, application No. 11/128,686, which is a continuation-in-part of application No. 10/156,315, filed on May 28, 2002, now Pat. No. 7,507,235, which is a continuation of application No. 09/879,294, filed on Jun. 12, 2001, now Pat. No. 6,447,443, application No. 11/128,686, which is a continuation-in-part of application No. 10/643,299, filed on Aug. 19, 2003, now Pat. No. 7,338,434.

(60) Provisional application No. 60/571,182, filed on May 14, 2004, provisional application No. 60/261,343, filed on Jan. 13, 2001, provisional application No. 60/263,739, filed on Jan. 24, 2001, provisional application No. 60/282,029, filed on Apr. 6, 2001, provisional application No. 60/286,952, filed on Apr. 26, 2001, provisional application No. 60/424,234, filed on Nov. 6, 2002, provisional application No. 60/404,969, filed on Aug. 21, 2002.

(51) Int. Cl.
*A61N 7/02* (2006.01)
(52) U.S. Cl. .......................................... 607/27; 607/28
(58) Field of Classification Search ............. 606/27–30; 600/201, 205, 210, 232, 235
See application file for complete search history.

(56) References Cited

U.S. PATENT DOCUMENTS 3,736,936 A 6/1973 Basiulis et al.

(Continued)

FOREIGN PATENT DOCUMENTS

EP 1 095 627 5/2001

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Roy D Gibson
(74) *Attorney, Agent, or Firm*—Mike Jaro; Jeffrey J. Hohenshell

(57) ABSTRACT

A method of thermal ablation using high intensity focused ultrasound energy includes the steps of positioning one or more ultrasound emitting members within a patient, emitting ultrasound energy from the one or more ultrasound emitting members, focusing the ultrasound energy, ablating with the focused ultrasound energy to form an ablated tissue area and removing the ultrasound emitting member.

26 Claims, 12 Drawing Sheets

U.S. PATENT DOCUMENTS

| | | |
|---|---|---|
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,562,900 A | 1/1986 | Anderson et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,010,886 A | 4/1991 | Passafaro et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,309,896 A | 5/1994 | Moll et al. |
| 5,314,466 A | 5/1994 | Stern et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,334,181 A | 8/1994 | Rubinsky et al. |
| 5,334,193 A | 8/1994 | Nardella |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,402,792 A | 4/1995 | Kimura |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,413,550 A | 5/1995 | Castel |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,437,664 A | 8/1995 | Cohen et al. |
| 5,441,499 A | 8/1995 | Fritzsch |
| 5,443,463 A | 8/1995 | Stern et al. |
| 5,443,470 A | 8/1995 | Stern et al. |
| 5,448,994 A | 9/1995 | Iinuma |
| 5,450,843 A | 9/1995 | Moll et al. |
| 5,452,582 A | 9/1995 | Longsworth |
| 5,452,733 A | 9/1995 | Sterman et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,492,126 A * | 2/1996 | Hennige et al. ............ 600/439 |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates |
| 5,560,362 A | 10/1996 | Sliwa, Jr. et al. |
| 5,562,720 A | 10/1996 | Stern et al. |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |

| | | | | | |
|---|---|---|---|---|---|
| 5,617,854 A | 4/1997 | Munsif | 5,904,711 A | 5/1999 | Flom et al. |
| 5,630,837 A | 5/1997 | Crowley | 5,906,580 A | 5/1999 | Kline-Schoder et al. |
| 5,637,090 A | 6/1997 | McGee et al. | 5,906,587 A | 5/1999 | Zimmon |
| 5,643,197 A | 7/1997 | Brucker et al. | 5,906,606 A | 5/1999 | Chee et al. |
| 5,656,029 A | 8/1997 | Imran et al. | 5,908,029 A | 6/1999 | Knudson et al. |
| 5,658,278 A | 8/1997 | Imran et al. | 5,916,213 A | 6/1999 | Haissaguerre et al. |
| 5,671,747 A | 9/1997 | Connor | 5,916,214 A | 6/1999 | Cosio et al. |
| 5,673,695 A | 10/1997 | McGee et al. | 5,921,924 A | 7/1999 | Avitall |
| 5,676,662 A | 10/1997 | Fleischhacker et al. | 5,921,982 A | 7/1999 | Lesh et al. |
| 5,676,692 A | 10/1997 | Sanghvi et al. | 5,927,284 A | 7/1999 | Borst et al. |
| 5,676,693 A | 10/1997 | LaFontaine | 5,928,191 A | 7/1999 | Houser et al. |
| 5,678,550 A | 10/1997 | Bassen et al. | 5,931,810 A | 8/1999 | Grabek |
| 5,680,860 A | 10/1997 | Imran | 5,931,848 A | 8/1999 | Saadat |
| 5,681,278 A | 10/1997 | Igo et al. | 5,954,661 A | 9/1999 | Greenspon et al. |
| 5,681,308 A | 10/1997 | Edwards et al. | 5,971,980 A | 10/1999 | Sherman |
| 5,687,723 A | 11/1997 | Avitall | 5,971,983 A | 10/1999 | Lesh |
| 5,687,737 A | 11/1997 | Branham et al. | 5,993,447 A | 11/1999 | Blewett et al. |
| 5,688,267 A | 11/1997 | Panescu et al. | 6,006,134 A | 12/1999 | Hill et al. |
| 5,690,611 A | 11/1997 | Swartz et al. | 6,007,499 A | 12/1999 | Martin et al. |
| 5,697,536 A | 12/1997 | Eggers et al. | 6,012,457 A | 1/2000 | Lesh |
| 5,697,882 A | 12/1997 | Eggers et al. | 6,016,811 A | 1/2000 | Knopp et al. |
| 5,697,925 A | 12/1997 | Taylor | 6,042,556 A | 3/2000 | Beach et al. |
| 5,697,927 A | 12/1997 | Imran et al. | 6,056,745 A | 5/2000 | Panescu et al. |
| 5,697,928 A | 12/1997 | Walcott et al. | 6,063,081 A | 5/2000 | Mulier |
| 5,713,831 A | 2/1998 | Olsson et al. | 6,071,279 A | 6/2000 | Whayne et al. |
| 5,713,942 A | 2/1998 | Stern | 6,088,894 A | 7/2000 | Oakley |
| 5,716,389 A | 2/1998 | Walinsky et al. | 6,096,037 A | 8/2000 | Mulier |
| 5,718,241 A | 2/1998 | Ben-Haim et al. | 6,113,592 A | 9/2000 | Taylor |
| 5,718,701 A | 2/1998 | Shai et al. | 6,117,101 A | 9/2000 | Diederich et al. |
| 5,720,775 A | 2/1998 | Larnard | 6,120,496 A | 9/2000 | Whayne et al. |
| 5,722,402 A | 3/1998 | Swanson et al. | 6,142,993 A | 11/2000 | Whayne et al. |
| 5,728,094 A | 3/1998 | Edwards | 6,142,994 A | 11/2000 | Swanson et al. |
| 5,730,074 A | 3/1998 | Peter | 6,146,379 A | 11/2000 | Fleischman |
| 5,730,127 A | 3/1998 | Avitall | 6,152,920 A | 11/2000 | Thompson et al. |
| 5,730,704 A | 3/1998 | Avitall | 6,161,543 A | 12/2000 | Cox et al. |
| 5,733,280 A | 3/1998 | Avitall | 6,165,174 A | 12/2000 | Jacobs et al. |
| 5,735,280 A | 4/1998 | Sherman et al. | 6,217,528 B1 | 4/2001 | Koblish et al. |
| 5,735,290 A | 4/1998 | Sterman et al. | 6,217,576 B1 | 4/2001 | Tu et al. |
| 5,755,760 A | 5/1998 | Maguire et al. | 6,224,592 B1 | 5/2001 | Eggers et al. |
| 5,762,066 A * | 6/1998 | Law et al. .................. 600/439 | 6,231,518 B1 | 5/2001 | Grabek et al. |
| 5,769,846 A | 6/1998 | Edwards et al. | 6,235,024 B1 | 5/2001 | Tu |
| 5,782,828 A | 7/1998 | Chen et al. | 6,237,605 B1 | 5/2001 | Vaska et al. |
| 5,785,706 A | 7/1998 | Bednarek | 6,238,347 B1 | 5/2001 | Nix et al. |
| 5,788,636 A | 8/1998 | Curley | 6,238,393 B1 | 5/2001 | Mulier |
| 5,792,140 A | 8/1998 | Tu et al. | 6,245,061 B1 | 6/2001 | Panescu et al. |
| 5,797,960 A | 8/1998 | Stevens et al. | 6,245,064 B1 | 6/2001 | Lesh et al. |
| 5,800,428 A | 9/1998 | Nelson et al. | 6,245,065 B1 | 6/2001 | Panescu et al. |
| 5,800,482 A | 9/1998 | Pomeranz et al. | 6,251,092 B1 | 6/2001 | Qin et al. |
| 5,810,802 A | 9/1998 | Panescu et al. | 6,251,128 B1 | 6/2001 | Knopp et al. |
| 5,817,021 A | 10/1998 | Reichenberger et al. | 6,266,564 B1 | 7/2001 | Hill et al. |
| 5,827,216 A | 10/1998 | Igo et al. | 6,270,471 B1 | 8/2001 | Hechel et al. |
| 5,836,947 A | 11/1998 | Fleischman et al. | 6,293,943 B1 | 9/2001 | Panescu et al. |
| 5,840,030 A | 11/1998 | Ferek-Petric et al. | 6,296,619 B1 | 10/2001 | Brisken et al. |
| 5,844,349 A | 12/1998 | Oakley et al. | 6,302,880 B1 | 10/2001 | Schaer |
| 5,846,187 A | 12/1998 | Wells et al. | 6,311,692 B1 | 11/2001 | Vaska et al. |
| 5,846,191 A | 12/1998 | Wells et al. | 6,312,383 B1 | 11/2001 | Lizzi et al. |
| 5,849,028 A | 12/1998 | Chen | 6,314,962 B1 | 11/2001 | Vaska et al. |
| 5,871,523 A | 2/1999 | Fleischman et al. | 6,314,963 B1 | 11/2001 | Vaska et al. |
| 5,871,525 A | 2/1999 | Edwards et al. | 6,315,732 B1 | 11/2001 | Suorsa et al. |
| 5,873,845 A | 2/1999 | Cline et al. | 6,325,797 B1 | 12/2001 | Stewart et al. |
| 5,876,399 A | 3/1999 | Chia et al. | 6,328,736 B1 | 12/2001 | Mulier |
| 5,879,295 A | 3/1999 | Li et al. | 6,331,158 B1 * | 12/2001 | Hu et al. ..................... 600/232 |
| 5,879,296 A | 3/1999 | Ockuly et al. | 6,332,881 B1 | 12/2001 | Carner et al. |
| 5,881,732 A | 3/1999 | Sung et al. | 6,346,077 B1 * | 2/2002 | Taylor et al. ................ 600/204 |
| 5,882,346 A | 3/1999 | Pomeranz et al. | 6,358,248 B1 | 3/2002 | Mulier |
| 5,885,278 A | 3/1999 | Fleischman | 6,361,531 B1 | 3/2002 | Hissong |
| 5,893,848 A | 4/1999 | Negus et al. | 6,364,876 B1 | 4/2002 | Erb et al. |
| 5,895,417 A | 4/1999 | Pomeranz et al. | 6,368,275 B1 | 4/2002 | Sliwa et al. |
| 5,897,553 A | 4/1999 | Mulier | 6,371,955 B1 | 4/2002 | Fuimaono et al. |
| 5,897,554 A | 4/1999 | Chia et al. | 6,383,151 B1 | 5/2002 | Diederich et al. |
| 5,899,898 A | 5/1999 | Arless et al. | 6,385,472 B1 | 5/2002 | Hall et al. |
| 5,899,899 A | 5/1999 | Arless et al. | 6,398,792 B1 | 6/2002 | O'Connor |
| 5,902,289 A | 5/1999 | Swartz et al. | 6,409,720 B1 | 6/2002 | Hissong et al. |

| | | |
|---|---|---|
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,429,217 B1 | 8/2002 | Puskas |
| 6,430,426 B2 | 8/2002 | Avitall |
| 6,440,127 B2 | 8/2002 | McGovern et al. |
| 6,440,130 B1 | 8/2002 | Mulier |
| 6,443,952 B1 | 9/2002 | Mulier |
| 6,447,443 B1 | 9/2002 | Keogh et al. |
| 6,447,507 B1 | 9/2002 | Bednarek et al. |
| 6,451,013 B1 | 9/2002 | Bays et al. |
| 6,461,314 B1 | 10/2002 | Pant et al. |
| 6,461,956 B1 | 10/2002 | Hsuan et al. |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,479,523 B1 | 11/2002 | Puskas |
| 6,484,727 B1 | 11/2002 | Vaska et al. |
| 6,487,446 B1 | 11/2002 | Hill et al. |
| 6,488,680 B1 | 12/2002 | Francischelli |
| 6,502,575 B1 | 1/2003 | Jacobs et al. |
| 6,508,765 B2 | 1/2003 | Suorsa et al. |
| 6,508,774 B1 | 1/2003 | Acker et al. |
| 6,514,250 B1 | 2/2003 | Jahns |
| 6,527,767 B2 | 3/2003 | Wang et al. |
| 6,537,248 B2 | 3/2003 | Mulier |
| 6,542,774 B2 | 4/2003 | Hill et al. |
| 6,558,382 B2 | 5/2003 | Jahns |
| 6,575,956 B1 | 6/2003 | Brisken et al. |
| 6,584,360 B2 | 6/2003 | Francischelli |
| 6,585,732 B2 | 7/2003 | Mulier |
| 6,595,934 B1 | 7/2003 | Hissong et al. |
| 6,605,084 B2 | 8/2003 | Acker et al. |
| 6,610,054 B1 | 8/2003 | Edwards et al. |
| 6,610,055 B1 | 8/2003 | Swanson et al. |
| 6,610,060 B2 | 8/2003 | Mulier |
| 6,613,048 B2 | 9/2003 | Mulier |
| 6,626,855 B1 | 9/2003 | Weng et al. |
| 6,628,987 B1 | 9/2003 | Hill et al. |
| 6,635,054 B2 * | 10/2003 | Fjield et al. .................... 606/27 |
| 6,645,199 B1 | 11/2003 | Jenkins et al. |
| 6,648,883 B2 | 11/2003 | Francischelli |
| 6,656,175 B2 | 12/2003 | Francischelli |
| 6,656,960 B2 | 12/2003 | Puskas |
| 6,663,627 B2 | 12/2003 | Francischelli |
| 6,690,973 B2 | 2/2004 | Hill et al. |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,718,208 B2 | 4/2004 | Hill et al. |
| 6,719,694 B2 | 4/2004 | Weng et al. |
| 6,735,471 B2 | 5/2004 | Hill et al. |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,778,854 B2 | 8/2004 | Puskas |
| 6,807,968 B2 | 10/2004 | Francischelli |
| RE38,654 E | 11/2004 | Hill et al. |
| 6,827,715 B2 | 12/2004 | Francischelli |
| RE38,705 E | 2/2005 | Hill et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,904,318 B2 | 6/2005 | Hill et al. |
| 6,911,019 B2 | 6/2005 | Mulier |
| 6,912,419 B2 | 6/2005 | Hill et al. |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 7,058,447 B2 | 6/2006 | Hill et al. |
| 7,072,720 B2 | 7/2006 | Puskas |
| 7,142,910 B2 | 11/2006 | Puskas |
| 7,184,828 B2 | 2/2007 | Hill et al. |
| 7,184,829 B2 | 2/2007 | Hill et al. |
| 7,338,434 B1 | 3/2008 | Haarstad et al. |
| 2002/0095139 A1 | 7/2002 | Keogh et al. |
| 2002/0138109 A1 | 9/2002 | Keogh et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Chrisitian |
| 2006/0229594 A1 | 10/2006 | Francischelli |
| 2008/0039746 A1 | 2/2008 | Hissong |

FOREIGN PATENT DOCUMENTS

| | | |
|---|---|---|
| EP | 1 750 804 | 7/2008 |
| WO | 01-080755 | 11/2001 |
| WO | 2005-113068 | 12/2005 |
| WO | 2007-067945 | 6/2007 |
| WO | 2007-140331 | 12/2007 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.
Sealy, "Direct Surgical Treatment of Arrhythmias: The Last Frontier in Surgical Cardiology," Chest 75(5): 536-537, 1979.
Sealy, "The Evolution of the Surgical Methods for Interruption of Right Free Wall Kent Bundles," The Annals of Thoracic Surgery 36(1): 29-36, 1983.
Guiraudon et al., "Surgical Repair of Wolff-Parkinson-White Syndrome: A New Closed-Heart Techique," The Annals of Thoracic Surgery 37(1): 67-71, 1984.
Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71:483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Surgical treatment of atrial fibrillation: a review; Europace (2004) 5, S20-S29 (abstract only).

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3945.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 ½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

Siefert et al., Radiofrequency Maze Ablation for Atrial Fibrillation, Circulation 90(4):I-594. Admitted published in the U.S. more than one year prior to earliest effective filing date of present application.

U.S. Appl. No. 60/123,505, filed Mar. 9, 1999.

\* cited by examiner

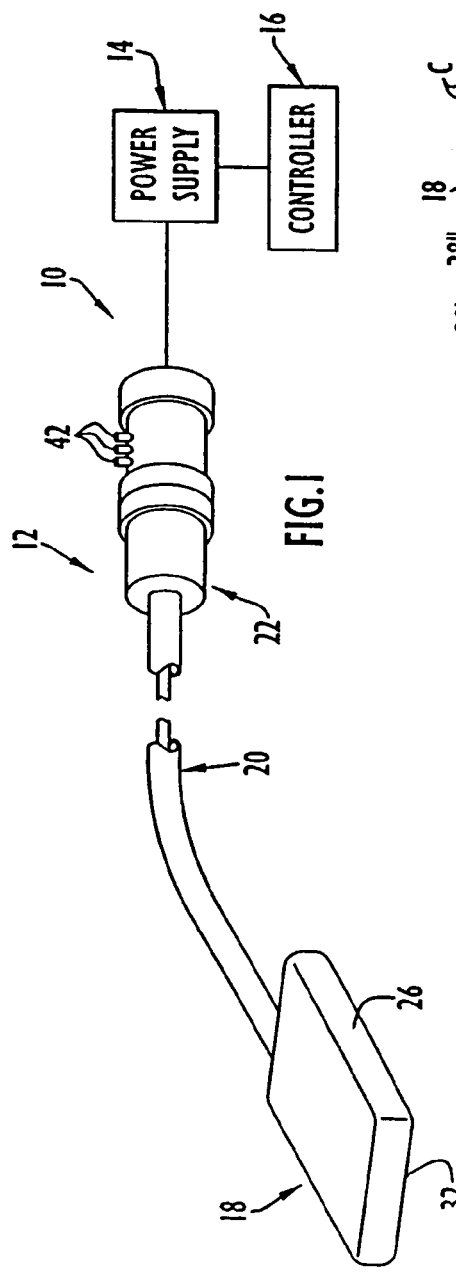
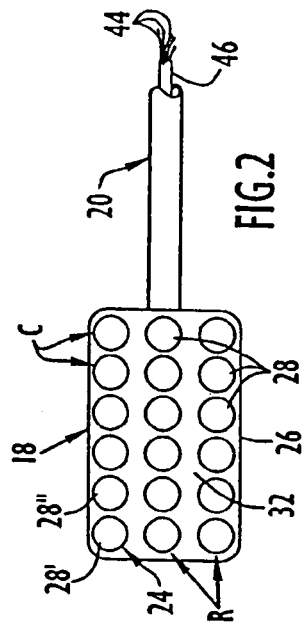
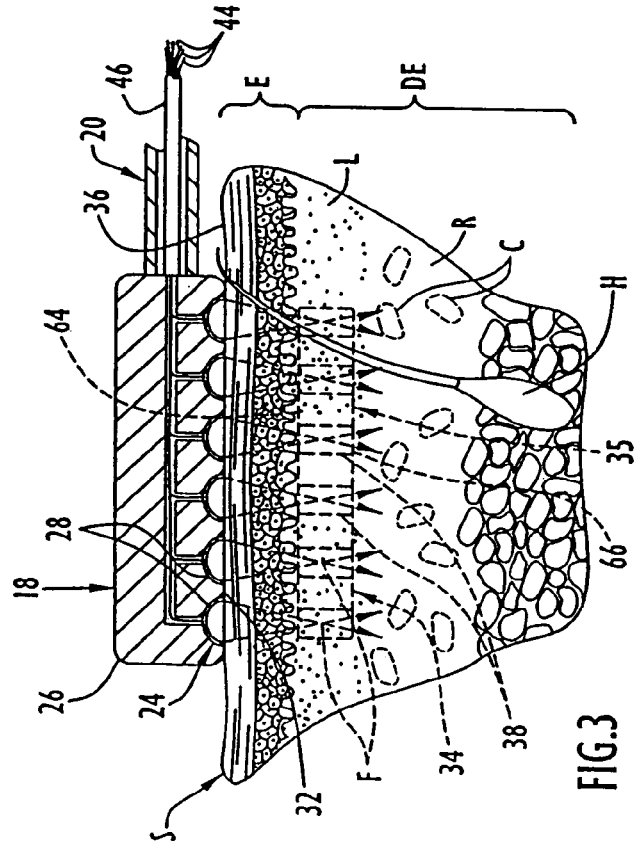
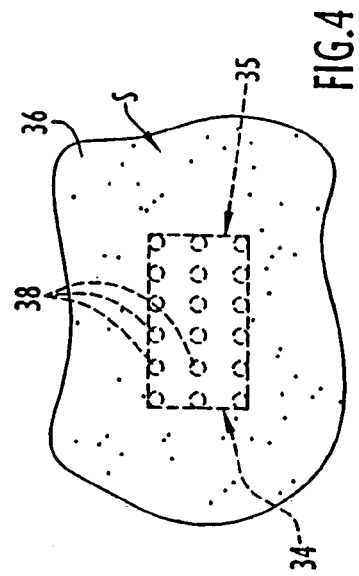

METHODS OF USING HIGH INTENSITY FOCUSED ULTRASOUND TO FORM AN ABLATED TISSUE AREA

CROSS-REFERENCE TO RELATED PATENT APPLICATIONS

This application claims the benefit of the filing date of co-pending U.S. Provisional Patent Application Ser. No. 60/571,182 filed on May. 14, 2004, the disclosure of which is incorporated herein by reference in its entirety.

This application is a continuation-in-part of U.S. patent application Ser. No. 10/464,213 filed Jun. 18, 2003, now U.S. Pat. No. 6,936,046, which is a continuation of U.S. patent application Ser. No. 09/629,194 filed Jul. 31, 2000, now U.S. Pat. No. 6,595,934, which is a continuation-in-part of U.S. patent application Ser. No. 09/487,705 filed Jan. 19, 2000, now abandoned, the disclosures of Which are incorporated herein by reference.

This application is also a continuation-in-part of U.S. patent application Ser. No. 10/156,315 filed May 28, 2002, now U.S. Pat. No. 7,507,235, which is a continuation of U.S. patent application Ser. No. 09/879,294 filed Jun. 12, 2001, now U.S. Pat. No. 6,447,443, which claims the benefit of the filing dates of U.S. Provisional patent applications Ser. No. 60/261,343 filed Jan. 13, 2001, Ser. No. 60/263,739 filed Jan. 24, 2001, Ser. No. 60/282,029 filed Apr. 6, 2001 and Ser. No. 60/286,952 filed Apr. 26, 2001,the disclosures of which are incorporated herein by reference.

This application is a continuation-in-part of U.S. patent application Ser. No. 10/643,299 filed Aug. 19, 2003, now U.S. Pat. No. 7,338,434, which claims the benefit of the filing dates of U.S. Provisional Patent Applications Ser. No. 60/424,243 filed Nov. 6, 2002 and Ser. No. 60/404,969 filed Aug. 21, 2002, the disclosures of which are incorporated herein by reference.

BACKGROUND OF THE INVENTION

1. Field of the Invention

The present invention relates generally to the treatment of anatomical tissue of a patient with ultrasound energy and, more particularly, to the ablation of tissue using high intensity focused ultrasound energy.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. In order to produce thermal effects in anatomical tissue, ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium, stand-off and/or sheath. By focusing the ultrasound energy at one or more specific focusing zones within the tissue, thermal effect can be confined to a defined location, region, volume or area, and such location, region, volume or area can be remote from the ultrasound emitting member.

With the use of high intensity focused ultrasound (HIFU), one or more focusing zones at or within a designated target location, region, volume or area within a larger mass, body or area of anatomical tissue can be subjected to high intensity ultrasound energy while tissue surrounding the target area is subjected to much lower intensity ultrasound energy. In this manner, tissue in the target area can be heated to a sufficiently high temperature so as to cause a desired thermal effect such as tissue damage, ablation, coagulation, denaturation, destruction or necrosis while tissue surrounding the target area is not heated to damaging temperatures and, therefore, is preserved. Heating of tissue in a target location, volume, region or area to an ablative temperature creates an ablative lesion in the tissue in the target location, volume, region or area that is desirable in the treatment of various medical conditions, disorders or diseases. For example, the lesion may remain as tissue having altered characteristics or may be naturally degraded and absorbed by the patient's body and thusly eliminated such that the remaining body, mass or area of tissue is of smaller volume or size due to the absence of the ablated tissue.

The use of high intensity focused ultrasound to eliminate tissue or to alter the characteristics of tissue in a target location, volume, region or area within a larger mass, body or area of anatomical tissue presents many advantages including minimization of trauma and pain for the patient, elimination of the need for a surgical incision, stitches and exposure of internal tissue, avoidance of damage to tissue other than that which is to be treated, altered or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various devices and/or methods for treating anatomical tissue with ultrasound have been proposed as represented by U.S. Patent Application Publication No. 2005/0080469 to Larson et al. and U.S. Pat. No. 6,858,026 to Sliwa et al., No. 6,840,936 to Sliwa et al., No. 6,805,129 to Pless et al. and No. 6,805,128 to Pless et al., No. 6,413,254 to Hissong et al., No. 6,361,531 to Hissong, No. 6,409,720 to Hissong, No. 6,451,013 to Bays et al., Re. 33,590 to Dory, No. 3,990,452 to Murry et al., No. 4,658,828 to Dory, No. 4,807,633 to Fry, No. 4,858,613 to Fry et al., No. 4,951,653 to Fry et al., No. 4,955,365 to Fry et al., No. 5,033,456 to Pell et al., No. 5,036,855 to Fry et al., No. 5,054,470 to Fry et al., No. 5,065,761 to Pell, No. 5,080,101 to Dory, No. 5,080,102 to Dory, No. 5,117,832 to Sanghvi et al., No. 5,134,988 to Pell et al., No. 5,143,074 to Dory, No. 5,150,711 to Dory, No. 5,150,712 to Dory, No. 5,158,070 to Dory, No. 5,222,501 to Ideker et al, No. 5,267,954 to Nita, No. 5,269,291 to Carter, No. 5,269,297 to Weng et al, No. 5,295,484 to Marcus et al, No. 5,304,115 to Pflueger et al., No. 5,312,328 to Nita et al., No. 5,318,014 to Carter, No. 5,342,292 to Nita et al., No. 5,354,258 to Dory, No. 5,380,274 to Nita, No. 5,391,197 to Burdette et al., No. 5,397,301 to Pflueger et al., No. 5,409,002 to Pell, No. 5,417,672 to Nita et al., No. 5,431,621 to Dory, No. 5,431,663 to Carter, No. 5,447,509 to Mills et al., No. 5,474,530 to Passafaro et al., No. 5,492,126 to Hennige et al., No. 5,501,655 to Rolt et al., No. 5,520,188 to Hennige et al., No. 5,542,917 to Nita et al., No. 5,620,479 to Diederich, No. 5,676,692 to Sanghvi et al., No. 5,728,094 to Edwards, No. 5,730,719 to Edwards, No. 5,733,315 to Burdette et al., No. 5,735,280 to Sherman et al., No. 5,738,114 to Edwards, No. 5,746,224 to Edwards, No. 5,762,066 to Law et al, No. 5,800,379 to Edwards, No. 5,800,429 to Edwards, No. 5,800,482 to Pomeranz et al, No. 5,807,308 to Edwards, No. 5,817,049 to Edwards, No. 5,823,197 to Edwards, No. 5,827,277 to Edwards, No. 5,843,077 to Edwards, No. 5,871,524 to Knowlton, No. 5,873,845 to Cline et al., No. 5,873,902 to Sanghvi et al., No. 5,879,349 to Edwards, No. 5,882,302 to Driscoll, Jr. et al., No. 5,895,356 to Andrus et al, No. 5,928,169 to Schatzle et al. and No. 5,938,608 to Bieger et al.

In particular, the use of high intensity focused ultrasound to thermally damage, ablate, coagulate, denature, cauterize, necrotize or destroy a target volume of tissue is exemplified by U.S. Patent Application Publication No. 2005/0080469 to Larson et al. and U.S. Pat. No. 6,858,026 to Sliwa et al., No. 6,840,936 to Sliwa et al., No. 6,805,129 to Pless et al. and No. 6,805,128 to Pless et al., No. 6,413,254 to Hissong et al., No. 6,361,531 to Hissong, No. 6,409,720 to Hissong, No. 6,451,013 to Bays et al., No. Re. 33,590 to Dory, No. 4,658,828 to Dory, No. 4,807,633 to Fry, No. 4,858,613 to Fry et al., No. 4,951,653 to Fry et al., No. 4,955,365 to Fry et al., No. 5,036,855 to Fry et al., No. 5,054,470 to Fry et al., No. 5,080,101 to Dory, No. 5,080,102 to Dory, No. 5,117,832 to Sanghvi et al., No. 5,143,074 to Dory, No. 5,150,711 to Dory, No. 5,150,712 to Dory, No. 5,295,484 to Marcus et al., No. 5,354,258 to Dory, No. 5,391,197 to Burdette et al., No. 5,431,621 to Dory, No. 5,492,126 to Hennige et al., No. 5,501,655 to Rolt et al., No. 5,520,188 to Hennige et al, No. 5,676,692 to Sanghvi et al, No. 5,733,315 to Burdette et al, No. 5,762,066 to Law et al., No. 5,871,524 to Knowlton, No. 5,873,845 to Cline et al, No. 5,873,902 to Sanghvi et al., No. 5,882,302 to Driscoll, Jr. et al., No. 5,895,356 to Andrus et al., No. 5,928,169; to Schätzle et al, and No. 5,938,608 to Bieger et al.

Heart arrhythmias, such as atrial fibrillation, have been treated by surgery. For example, a surgical procedure called the "Maze" procedure was designed to eliminate atrial fibrillation permanently. The procedure employs incisions in the right and left atria which divide the atria into electrically isolated portions which in turn results in an orderly passage of the depolarization wave front from the sino-atrial node (SA Node) to the atrial-ventricular node (AV Node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing ultrasound devices or other types of ablation devices, e.g. thermal ablation, micro-wave ablation, RF ablation, cryo-ablation or the like to ablate tissue along pathways approximating the incisions of the Maze procedure. Electrosurgical systems for performing such procedures are described in U.S. Pat. No. 5,916,213 to Haissaguerre, et al., U.S. Pat. No. 5,957,961 to Maguire, et al. and U.S. Pat. No. 5,690,661, all incorporated herein by reference in their entireties. Procedures are also disclosed in U.S. Pat. No. 5,895,417 to Pomeranz, et al, U.S. Pat. No. 5,575,766 to Swartz, et al., U.S. Pat. No. 6,032,077 to Pomeranz, U.S. Pat. No. 6,142,994 to Swanson, et al. and U.S. Pat. No. 5,871,523 to Fleischman, et al., all incorporated herein by reference in their entireties. Cryo-ablation systems for performing such procedures are described in U.S. Pat. No. 5,733,280 to Avitall, also incorporated herein by reference in its entirety. High intensity focused ultrasound systems for performing such procedures are described in U.S. Patent Application Publication No. 2005/0080469 to Larson et al. and U.S. Pat. No. 6,858,026 to Sliwa et al., No. 6,840,936 to Sliwa et al., No. 6,805,129 to Pless et al. and No. 6,805,128 to Pless et al., all incorporated herein by reference in their entireties.

High intensity focused ultrasound is an attractive surgical ablation modality as the energy can be focused to create heat at some distance from the transducer. In epicardial applications, most of the heat loss is to the blood, which is also some distance from the transducer. This is in contrast to most other technologies, in which heating occurs close to the transducer (or electrode) and deeper heating is by thermal conduction. Additionally, since the coronary arteries are typically towards the epicardial surface, they are theoretically less susceptible to heating and subsequent constriction by a device such as a HIFU device, which can generate heat deep within the myocardium. For example, a non-irrigated RF epicardial ablation approaches has the highest heating occurring at the epicardial surface. Any transfer of heat to the deeper endocardium is by thermal conduction. Irrigated RF epicardial ablation approaches allow the heat to penetrate deeper into the tissue, but are nonetheless limited in depth. In contrast, a HIFU approach can focus the energy to generate heat deeper within the tissue at a substantial distance from the transducer.

Another therapeutic method to terminate AF is to ablate an area that is sufficiently large enough such that there is not enough critical mass to sustain the reentrant waveform characteristic of the arrhythmia.

In conjunction with the use of ablation devices, various control mechanisms have been developed to control delivery of ablation energy to achieve the desired result of ablation, i.e. killing of cells at the ablation site while leaving the basic structure of the organ to be ablated intact. Such control systems may include measurement of temperature and/or impedance at or adjacent to the ablation site, as are disclosed in U.S. Pat. No. 5,540,681 to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 to Marchlinski et al., incorporated herein by reference in its entirety. Alternatively, detection of an impedance rise or an impedance rise following an impedance fall are disclosed in U.S. Pat. No. 5,558,671 to Yates and U.S. Pat. No. 5,540,684 to Hassler, respectively, also incorporated herein by reference in their entireties.

Three basic approaches have been employed to create elongated lesions using ablation devices. The first approach is simply to create a series of short lesions using a contact electrode, moving it along the surface of the organ wall to be ablated to create a linear lesion. This can be accomplished either by making a series of lesions, moving the electrode between lesions or by dragging the electrode along the surface of the organ to be ablated and continuously applying ablation energy, as described in U.S. Pat. No. 5,897,533 to Mulier, et al., incorporated herein by reference in its entirety. The second basic approach to creation of elongated lesions is simply to employ an elongated electrode, and to place the elongated electrode along the desired line of lesion along the tissue. This approach is described in U.S. Pat. No. 5,916,213, cited above. The third basic approach to creation of elongated lesions is to provide a series of electrodes and arrange the series of electrodes along the desired line of lesion. The electrodes may be activated individually or in sequence, as disclosed in U.S. Pat. No. 5,957,961, also cited above. In the case of multi-electrode devices, individual feedback regulation of ablated energy applied via the electrodes may also be employed.

SUMMARY OF THE INVENTION

Accordingly, it is a primary object of the present invention to overcome the various disadvantages of prior methods of treatment of AF.

It is also an object of the present invention to ablate tissue using high intensity focused ultrasound to treat AF.

Another object of the present invention is to utilize high intensity focused ultrasound to perform one or more lesions of a Maze procedure.

Another object of the present invention is to utilize high intensity focused ultrasound to ablate a substantial portion of the atria in order to "debulk" the chamber such that the substrate is modified sufficiently to prevent the maintenance of AF.

Another object of the present invention is to ablate the parasympathetic neurons and/or the autonomic ganglia and their regions of innervation of the heart such that the neural impulses promoting AF are blocked.

Another object of the present invention is to ablate specific locations within the heart that are responsible for initiating arrhythmias. These locations are often referred to as "triggers".

Still further, the present invention has as an object to use high intensity focused ultrasound energy, emitted by an ultrasound-emitting member placed within the esophagus, the trachea, the vasculature, against a surface of the heart, and/or in a trans-thoracic approach from outside the chest, for example, to form one or more lesions of a Maze procedure. Alternatively, an ultrasound-emitting member may be placed within the thoracic cavity such as intercostally or subcostally as well as by a sub-xiphoid approach.

It is still another object of the present invention to have an organ positioning system and method that comprises a device that engages organ tissue and allows a surgeon to easily position, manipulate, stabilize and/or hold an organ during a high intensity focused ultrasound ablation procedure.

It is still another object of the present invention to place a hand-held high intensity focused ultrasound device on the epicardial surface of the heart and ablate tissue. The ultrasound energy delivered by the device may be focused at a distance from the device to ablate the underlying myocardium without affecting the coronary arteries and sinus. Such a device may be used to ablate the left atrial isthmus, as well as other lesions, for example Maze-type lesions.

Another object of the present invention is to temporarily and controllably start and stop the heart during a high intensity focused ultrasound ablation procedure. For example, controlled intermittent asystole (CIA) may be used to control or inhibit motion associated with cardiac contraction such that a relatively stationary volume of cardiac tissue may be targeted with high intensity focused ultrasound. Cardiac and/or respiration gating may also be used during an ablation procedure.

Another object of the present invention is to have an organ positioning system and method that comprises a device that engages organ tissue and allows a surgeon to easily position, manipulate, stabilize and/or hold an organ during a controlled intermittent asystole, high intensity focused ultrasound ablation procedure.

Some of the advantages of the present invention are that varying intensity levels of ultrasound energy can be delivered to tissue for varying periods of time depending on desired ablative effect, the duration of ultrasound energy delivery or application to the tissue needed to accomplish a desired effect may be relatively brief depending on desired size for the lesions of the ablated tissue area and/or desired thermal effect on the tissue, the transducer or other member used to emit the ultrasound energy may be stationary or may be movable, or may be a microprocessor-controlled phased array in order to scan a target area with focused ultrasound, a plurality of individual ablated tissue areas can be formed in the tissue with the ablated tissue areas being separate and discontinuous or being contacting, abutting, contiguous or overlapping to form a single continuous ablated tissue area of desired size and/or shape, the ultrasound emitting member can remain stationary or can be moved along to scan a target area with focused ultrasound, the transducer or other member may be designed with a focusing configuration designed to ensure that the lesions of the ablated tissue area have a desired cross-sectional size, begin a desired depth within the tissue and have a desired depth, the transducer or other member is positioned externally adjacent or in contact with an external surface of the tissue or is acoustically coupled with the tissue to form an internal ablated tissue area without damaging the tissue surface and, in particular, a body cavity such as the esophagus or trachea, and an ablated tissue area of definitive size can be repeatedly and consistently produced. The esophagus is close to the posterior of the left atrium of the heart. This position makes it particularly attractive for trans-esophageal echocardiography (TEE) imaging as well as trans-esophageal ultrasound ablation.

The transducers of a phased array may be electronically controlled such that individual transducers can be controlled to interfere with the adjacent transducers. This interference can be used to "steer" the focal point of the acoustical energy to virtually any spot. For example, each element may be independently controlled and energized slightly out of phase with one another to electronically steer the focal point.

These and other objects, advantages and benefits are realized with the present invention as generally characterized in a method of tissue ablation using high intensity focused ultrasound wherein ultrasound energy is emitted from the ultrasound emitting member into the tissue to be ablated. The ultrasound energy is focused within the tissue at one or more overlapping or non-overlapping focusing zones contained in a target area. If multiple focusing zones are desired, the focusing zones are spaced from one another and, due to focusing of the ultrasound energy at the focusing zones, the ultrasound energy is of higher or greater intensity in the tissue at the focusing zones than in the tissue surrounding the focusing zones. The tissue is heated at the focusing zones by the focused ultrasound energy, thereby forming an ablated tissue area. Once an ablated tissue area of desired extent has been obtained, the ultrasound emitting member is removed.

The ultrasound emitting member has a focusing configuration causing the ultrasound energy to be focused a predetermined distance from an active face of the ultrasound emitting member. Also, the focusing configuration results in formation of lesions of predetermined or known depth in accordance with the length of the focusing zones, the selected ultrasound energy intensities and frequencies and the selected duration times for ultrasound energy delivery. The lesion depths are selected so that the lesions do not extend deeper than desired, thereby avoiding unwanted damage to surrounding tissue. The plurality of lesions may be non-contacting, with each lesion surrounded by unablated tissue. One or more of the plurality of lesions may contact another one of the plurality of lesions. The cross-sectional size of the lesions and the location and arrangement of the focusing zones in the tissue result in formation of a specific size ablated tissue area having a specific cross-sectional configuration. A single, discrete ablated tissue area or a plurality of single, discrete ablated tissue areas can be formed in the tissue in a single procedure or treatment performed at one time or in multiple procedures or treatments performed at different times. Where a plurality of ablated tissue areas are formed, the ablated tissue areas can be contiguous, contacting, overlapping or in abutment with one another so that the ablated tissue areas together form or create a single ablated tissue area of larger cross-sectional size and/or of a desired cross-sectional configuration.

One aspect of the present invention-provides a system for positioning, manipulating, holding, grasping, immobilizing and/or stabilizing an organ, such as a heart. The system may include one or more tissue-engaging devices, one or more suction sources, one or more fluid sources, one or more high intensity focused ultrasound energy devices, one or more sensors and one or more processors. The system may also include one or more imaging devices, guidance devices, drug delivery devices and/or illumination devices. A tissue-engaging device of the system may comprise a tissue-engaging head, a support apparatus and a clamping mechanism for attaching the tissue-engaging device to a stable object, such as a retractor that is fixed to a patient's chest or an operating table. A tissue-engaging device of the system may comprise one or more energy transfer elements connected to an energy source, one or more sensors connected to a processor, one or more suction openings connected to a suction source, and/or one or more fluid openings connected to a fluid source.

Another aspect of the present invention provides a method of positioning, manipulating, holding, grasping, immobilizing and/or stabilizing an organ, such as a heart. The method includes engaging and positioning an organ, such as a heart, during a high intensity focused ultrasound ablation procedure. The ablation procedure may include intermittently stimulating a vagal nerve and/or pacing a heart. The ablation procedure may include placement of a lead on or within a heart. The ablation procedure may include the use of suction to engage and position an organ, such as a heart. The ablation procedure may include the delivery of fluids, gases, and/or agents, such as drugs.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

BRIEF DESCRIPTION OF THE DRAWINGS

FIG. 1 is a broken perspective view, partly schematic, illustrating a high intensity focused ultrasound stimulation or ablation assembly for use in the methods of the present invention.

FIG. 2 is a broken bottom view of an ultrasound emitting member of a focused ultrasound ablation device of the high intensity focused ultrasound stimulation or ablation assembly.

FIG. 3 is a broken side view, partly in section, of the ultrasound emitting member and depicting focusing of ultrasound energy in tissue to form an ablated tissue area containing unablated tissue and a plurality of lesions at which the tissue is ablated.

FIG. 4 is a broken top view illustrating the surface or cross-sectional configuration of the ablated tissue area of FIG. 3.

DESCRIPTION OF THE PREFERRED EMBODIMENTS

Figure 7:
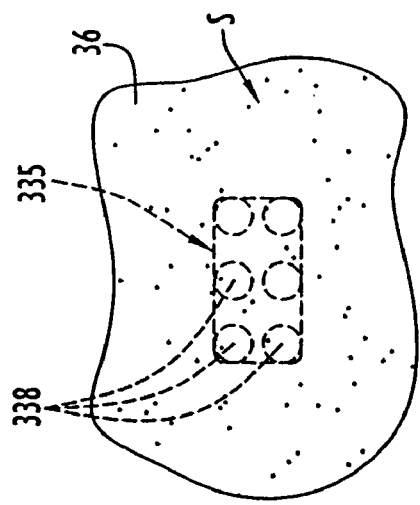
FIG. 7 is a broken top view illustrating the surface or cross-sectional configuration of another alternative ablated tissue area created in the tissue.

A high intensity focused ultrasound ablation or stimulation assembly or system 10 for use in the methods of the present invention is illustrated in FIG. 1 and is similar to the high intensity focused ultrasound stimulation assembly described in prior U.S. patent application Ser. No. 10/464,213 and U.S. patent application Ser. No. 10/600,871, the disclosures of which are incorporated herein by reference. The high intensity focused ultrasound ablation or stimulation assembly or system 10 includes a focused ultrasound ablation or stimulation device 12, a power supply 14 and a controller 16. The focused ultrasound ablation or stimulation device 12 is similar to that described in U.S. patent applications Ser. Nos. 10/464,213 and 10/600,871 and includes a focused ultrasound emitting member 18, an elongate handle shaft or body 20 having a distal end at which the ultrasound emitting member is disposed and a handle or handpiece 22 coupled to a proximal end of the handle shaft 20. As shown in FIGS. 2 and 3, the ultrasound emitting member includes a transducer 24 carried by or within a housing, carrier or case 26. The transducer, which includes one or more individual ultrasound emitting elements or transducer elements, is capable of generating and emitting ultrasound energy in response to being supplied with electrical power from power supply 14. In the case of ultrasound emitting member 18, the transducer includes a plurality of individual ultrasound emitting elements or transducer elements 28, each including a piezoelectric element that vibrates to produce ultrasound energy when an electrical potential or signal is supplied thereto. The transducer elements 28 have a focusing configuration or geometry that results in the ultrasound energy produced thereby being focused a fixed distance from the ultrasound emitting member. The transducer elements 28 have a partial spherical or concave configuration and/or include one or more lens causing the ultrasound energy generated thereby to be focused, as shown by arrows in FIG. 3, at focusing zones F, respectively.

The transducer elements 28 are arranged in an array on or in housing 26; and, therefore, the transducer 24 may be considered a multi-array transducer. In the case of ultrasound emitting member 18, the transducer elements are shown arranged in a planar array of three rows R and six columns C, although the transducer elements can be arranged in any number of rows and columns. Alternatively, the transducer elements may be angled to a more central area to create a lesion of a desired shape rather than in a row aimed along the same axis. In the case of focused ultrasound emitting member 18, each row R has an equal number of transducer elements, and each column C has an equal number of transducer elements. It should be appreciated that any number of transducer elements can be provided in each row and column and that the number of transducer elements provided in each row and column can be the same or different. Alternatively, the individual transducer element or elements mounted in the housing may be of an elongated or linear shape and may be largely aligned parallel with each other. Each of these linear elements would be capable of producing a line of focused energy.

The transducer elements 28 can be referenced by their location in the array. For example, the transducer element 28☐ in the first row, first column can be designated transducer element R1C1, the transducer element 28☐ in the first row, second column can be designated transducer element R1C2 and so on. The transducer elements may be disposed as close as possible to one another; however, it should be appreciated that the spacing between the individual transducer elements 28 of the array can vary so that adjacent transducer elements can be disposed closer together or further apart from one another. As explained further below, the transducer elements 28 are selectively, independently actuatable to selectively emit or not emit ultrasound energy.

The transducer elements 28 can be designed in various ways as known in the art. In the case of transducer 24, the transducer elements each comprise a piezoelectric element formed by a layer of piezoelectric material carried by housing 26. The piezoelectric elements are recessed from a planar external lower or bottom surface 32 of housing 26. The piezoelectric elements are curved in a direction inwardly of surface 32 such that ultrasound energy generated by the piezoelectric elements is emitted from focused ultrasound emitting member 18 in a direction perpendicular to surface 32 for focusing at the focusing zones F, which are spaced outwardly of surface 32. Accordingly, surface 32 is an active surface or face of the ultrasound emitting member which, when positioned externally on, adjacent or in contact with tissue S, results in the ultrasound energy emitted by the transducer being focused at zones F, which will be disposed within the tissue S as shown in FIG. 3. When the ultrasound emitting member is positioned on, against or adjacent the tissue S at a location aligned with a designated target area 34 within the tissue S, the target area 34 being shown in dotted lines in FIGS. 3 and 4, the focusing zones will be disposed at or within the target area as best shown in FIG. 3.

Each focusing zone F consists of a single point or a plurality of points forming a zone at which the ultrasound energy is focused. Each focusing zone is in line with a central axis of the corresponding transducer element. Each focusing zone is disposed a fixed predetermined distance from a plane containing the active face 32, the predetermined distance for each focusing zone being perpendicular or normal to the active face 32. Therefore, the focusing zones F will also be disposed a predetermined perpendicular distance or a calculable or determinable perpendicular distance from an external surface 36 of tissue S with which the active face 32 is placed in contact or adjacent thereto. Where the active face 32 is placed in contact with the external tissue surface 36, the perpendicular distance that zones F are disposed from external tissue surface 36 will be the same as the predetermined distance. Where the active face 32 is not placed in contact with the external tissue surface 36 but, rather, is spaced from the external tissue surface 36 by a known amount, for example, the perpendicular distance that zones F are disposed from the external tissue surface will correspond to the predetermined distance minus the distance that the active face 32 is spaced from the external tissue surface 36. Where the active face 32 is spaced from the external tissue surface 36, an acoustic coupling medium can be disposed between the external tissue surface 36 and the member 18. Examples of acoustic coupling mediums are disclosed in U.S. Patent Application Publication No. 2004/0234453 to Smith and U.S. Pat. No. 6,039,694 to Larson et al., both incorporated herein by reference in their entireties. Acoustic coupling mediums may include stand-offs and/or sheaths, which may contain a gel that can act as a heat sink for cooling and/or as a medium for energy transfer. The stand-offs and/or sheaths may be disposable. For example, a disposable condom-like sheath could be placed over the device end.

The individual transducer elements, 28 of ultrasound emitting member 18 may be individually controlled in a manner to interfere with one another such that the focal zone can be precisely controlled. For example, individual elements can be driven at the same frequency, but different phases and possibly different amplitudes to form a phased array transducer and focus the energy more exactly. The transducers may have varying focal lengths or frequencies at differing, converging angles. In one embodiment, a series of two or more transducers may be aimed at the same focal point but could be alternated on and off to reduce heat generation of the transducers and the tissue directly in front of them thus preventing near-field tissue necrosis. This on/off cycling technique would allow a lesion to be made more quickly without intermediate tissue damage. In one embodiment of the present invention, an ultrasound conductive cooling field may be created with a cooling liquid, for example, delivered between the transducer elements and the tissue.

Since the ultrasound is focused at focusing zones F, which may be spaced from one another, the ultrasound is of greater or higher intensity at focusing zones F than in tissue surrounding the focusing zones F. Ultrasound energy is thusly focused or concentrated at the focusing zones F, causing the tissue at the focusing zones F to be heated to an ablative temperature resulting in formation of lesions 38 at the focusing zones, respectively. The tissue is ablated at the lesions 38; and, as used herein, "ablated" tissue includes tissue that has been thermally damaged, altered, necrotized, denatured, destroyed, coagulated or cauterized. When all of the transducer elements 28 are actuated, as shown in FIG. 3, heating of tissue S will occur at a focusing zone F for each transducer element, resulting in formation of a lesion 38 at each focusing zone F. The cross-sectional size of the lesions will normally depend on the width of the focusing zones. However, depending on the intensity and duration of the ultrasound energy, the lesions 38 may "grow" or "spread" somewhat beyond the focusing zones due to thermal conduction causing the dispersal or spread of heat from the focusing zones. Therefore, depending on procedural parameters and the dimensions of the focusing zones, each lesion 38 has a predetermined or predictable cross-sectional size, i.e. length and width, as well as depth. As an example, each lesion 38 spreads radially outwardly somewhat from the corresponding focusing zone. The lesions 38 have a generally circular surface or cross-sectional configuration as shown in FIGS. 3 and 4 and a specific depth as shown in FIG. 3. Depending on procedural parameters, the dimensions of the focusing zones and/or the type of tissue being ablated, the lesions may or may not have a uniform cross-section along their depth. Where the focusing zones are sufficiently close together, and where the intensity of the ultrasound energy emitted from the transducer elements is sufficiently high and is applied to the tissue for a sufficient duration, the individual lesions may merge to form a single continuous lesion at the target area so that the target area is filled with ablated tissue. However, depending on the spacing between the focusing zones, and depending on the intensity of the ultrasound energy emitted from the transducer elements and the duration of ultrasound energy delivery to the tissue, the lesions 38 may remain separate, discrete and not connected to one another as shown in FIGS. 3 and 4 so that the target area 34 contains unablated tissue and the lesions 38 at which the tissue is ablated. FIG. 4 illustrates a lesion 38 formed in tissue S for each focusing zone F wherein the lesions 38 are disposed within the target area 34 but do not merge with, contact, overlap or abut one another. Rather, each lesion 38 is surrounded or circumscribed perimetrically by unablated tissue. The non-contacting lesions 38 and unablated tissue are contained in an ablated tissue area 35 at, coincident, coextensive or aligned with the target area 34.

When all of the transducer elements 28 are actuated, an ablated tissue area of specific surface or cross-sectional configuration and size is created within the tissue S for the transducer 24 in accordance with the configuration and size of the array, the intensity level of the emitted ultrasound energy, the duration or time of ultrasound energy delivery to the tissue, and the size of the lesions. Accordingly, an ablated tissue area having a specific cross-sectional length, width and depth is formed in the tissue, with the perimeter of the ablated tissue area circumscribing the array of lesions 38. FIGS. 3 and 4 illustrate, in dotted lines, the ablated tissue area 35 formed in tissue S when all of the transducer elements are actuated. The ablated tissue area 35 has a generally rectangular surface or cross-sectional configuration or area with a predetermined cross-sectional length and width shown in FIG. 4 and a predetermined cross-sectional depth, shown in FIG. 3, the cross-sectional depth corresponding to the depth of the lesions 38. When the ultrasound emitting member 18 is positioned on, against or adjacent the tissue S at a location aligned with a designated target area 34, the ablated tissue area 35 will be formed at or coincide with the target area as shown in FIGS. 3 and 4. The ablated tissue area is surrounded, bordered or circumscribed perimetrically by unablated tissue, as well as having unablated tissue above and below it. Since the focusing zones F begin the predetermined distance or the calculable or determinable distance below the tissue surface 36, the ablated tissue area 35 is an internal or subsurface ablated tissue area beginning the predetermined distance or the calculable or determinable distance beneath the tissue surface. Accordingly, the lesions 38 and ablated tissue area 35 begin at a beginning or starting margin 64 located the predetermined or calculable distance below the external tissue surface 36 and end at an ending margin 66 disposed further below the external tissue surface than the beginning margin, the distance between the beginning and ending margins corresponding to the depth of the lesions 38 and, therefore, the depth of the ablated tissue area 35.

The housing 26 can have various external configurations and sizes and can be formed by a portion of the transducer or can mount the transducer elements in various ways. The handle shaft 20 comprises an elongate, hollow or tubular member of sufficient length to position the ultrasound emitting member 18 at various operative sites in or on the body of a patient while the handle 22 is maintained at a remote location, typically externally of the patient's body. The handle shaft 20 could be solid and may comprise a bar or other shaped member. Preferably, the handle shaft 20 is malleable as disclosed in U.S. patent application Ser. No. 09/488,844, the disclosure of which is incorporated herein by reference. The handle 22 has a forward end coupled to the proximal end of handle shaft 20 and has a rearward end. The handle 22 preferably has a configuration to facilitate grasping by a surgeon or other operator. One or more controls or switches 42 may be provided on handle 22 to effect operation of the focused ultrasound ablation device. The line of focused energy F, may be aligned with the long axis of the entire device. Alternatively, the housing 26 may be attached to the handle shaft 20 such that housing 20 may be manually or remotely rotated such that the line of focused energy F, is perpendicular to the long axis of the device or some angle between perpendicular and parallel to the long axis of the device.

One or more electrical transmission wires 44 is/are connected to the transducer 24 and extend through the handle shaft 20 for connection with power supply 14 in order to transmit or supply electric current from the power supply to the transducer. The power supply may be disposed partly or entirely in the handle, or may be provided separately as a console or unit coupled to the handle shaft or the handle via one or more appropriate transmission wires, which may be the same or different from the one or more transmission wires 44. For example, an electrical cord of suitable length may be removably coupled between the handle 22 and the power supply 14. The power supply 14 can be designed in various ways as a source or supply of electricity to activate or excite transducer 24 to generate and emit ultrasound energy. For example, the power supply can be designed to provide high frequency alternating electrical current to the transducer via the one or more transmission wires. The power supply may include a single or multiple channel RF generator, with or without an amplifier, providing a current or voltage source to power the transducer(s). Electrical current provided by the power supply is selectively discharged into all or selected ones of the piezoelectric elements producing vibration of all or selected ones of the piezoelectric elements and, therefore, producing acoustic or ultrasonic waves or energy. The power supply may be separate from the handle but may be operated via controls 42 on the handle. In addition, the transducer assembly may incorporate air or liquid cooling circulation channels to remove excess internal heat generated during operation.

Each transducer element, 28 may have slightly different physical characteristics such as efficiency, focal zone, etc. that significantly affect performance. These variances can be compensated for by controller 16. The handle 22 may have incorporated within it, a memory chip that is capable of being read by controller 16. The memory chip may store transducer properties, such as power requirements, temperature requirements, number and/or type of transducers, type of device, number of allowed uses, reuse information, variation in device to device characteristics, etc. that were characterized and recorded during manufacture, assembly and/or use. The memory chip may store information delivered by controller 16. For example, the controller may deliver a date and time of use stamp to the memory chip and/or details about a procedure. The controller and/or memory chip may be used to prevent the use of the device for more times than desired or acceptable. One or more reuse prevention features may be incorporated into ablation system 10.

In the case of focused ultrasound ablation device 12, a transmission wire 44 is provided for each piezoelectric element and, therefore, for each transducer element. As shown in FIG. 3, each transmission wire 44 is connected to its corresponding piezoelectric element and to the power supply so that the transducer elements are individually driven by or supplied with current from the power supply. The transmission wires 44 are disposed in respective passages within the housing and may be disposed within a sheath or sleeve 46 extending through shaft 20. However, the transmission wires can be disposed externally of the housing and/or the shaft. The transmission wires 44 are connected to switches (not shown), respectively, for controlling the supply or transmission of current from the power supply 14 to the piezoelectric elements, respectively. The switches can be incorporated in the ultrasound emitting member 18, the power supply 14 and/or the controller 16.

The controller or control unit 16 controls the supply of power from power supply 14 to transducer 24 so that the transducer can be driven to deliver various intensity levels of ultrasound energy for various durations, periods or lengths of time. In particular, the controller 16 controls the supply of power from the power supply to the individual piezoelectric elements so that the transducer elements can be individually driven or actuated to emit ultrasound energy. The controller, which may be designed as part of the power supply, will typically include a control panel and display monitor, one or more switches for current control, an input mechanism such as a keyboard, and/or a microprocessor including memory, storage and data processing capabilities for performing various functions. The controller is capable of selectively activating the switches for the transducer elements to "fire" or effect actuation of all or selected ones of the plurality of transducer elements to emit ultrasound energy. For example, switches on the controller 16 and/or the controller keyboard can be used to selectively couple and decouple the individual transducer elements 28 with the electrical drive signal or current from the power supply 14.

Input to the controller 16 provided by the surgeon or other medical personnel determines the transducer elements 28 to be actuated. For example, data entered via the controller keyboard is used to identify the particular transducer elements to be actuated, the transducer elements being identified, for example, by their location or position in the array as explained above. In this manner, the switches of selected transducer elements can be activated to permit transmission of electrical current from the power supply to the piezoelectric elements of the selected transducer elements while the switches of other non-selected transducer elements can remain deactivated to prevent transmission of electrical current thereto when the power supply is actuated or switched to an "on" mode. It should be appreciated that various components and/or methodology can be incorporated in the device 12, the power supply 14 and/or the controller 16 to permit selective actuation of selected ones of the transducer elements 28 and that such components and/or methodology would be within the purview of one skilled in the art. In addition, the precise location to focus ablative energy can be determined by various imaging modalities such as ultrasound imaging, CT, MRI, PET, fluoroscopy, etc. The coordinates for the desired area of ablation from any of these imaging modalities can be electronically fed to controller 16 such that the desired ablation pattern can be generated and ablated. Two or three-dimensional imaging may be performed as well as phased or annular array imaging may be performed. For example, two or three-dimensional echocardiography, such as transesophageal echocardiography, or ultrasound imaging, such as transthoracic ultrasound imaging may be employed as described in U.S. Patent Application Publication No. 2005/0080469, the disclosure of which is incorporated by reference in its entirety.

Various transducers can be used in the methods of the present invention. The piezoelectric elements can be made of various piezoelectric materials such as PZT crystal materials, hard lead, zirconate/lead titanium, piezoelectric ceramic, or lithium-niobate piezoceramic material. The transducer elements can be of various sizes and can have various focusing geometries. The frequency ranges of the transducers can vary depending on clinical needs. Transducer frequencies may be in the range of 0.5 to 12 MHz and, more typically, in the range of 5 to 12 MHz. Preferably, the transducer frequency will allow thermal ablation of the tissue to be effected in response to the application or delivery of ultrasound energy to the tissue for a relatively short duration or length of time.

In accordance with the present invention, the duration or length of time for ultrasound energy delivery or application to the tissue preferably ranges from 2 to 60 seconds depending on desired lesion size and/or ablative effect.

In accordance with the methods of the present invention, high intensity focused ultrasound may used to create an ablated tissue area containing unablated tissue and a plurality of lesions at which the tissue is ablated.

As shown in FIG. 3, the ultrasound emitting member 18 is placed against the tissue S of a patient to position the active face 32 in contact with the external tissue surface 36. The active face is placed at or on the surface 36 at a location aligned with a desired target area 34 in the tissue for creation of an ablated tissue area, such location corresponding to an area of the tissue that is to be ablated. The shaft 20 may be grasped and manipulated, as necessary, to facilitate positioning of the active face at the desired location on the external tissue surface. Typically, the ultrasound emitting member will be placed in contact with tissue at a location where an ablation lesion is desired. Also, all or specific ones of the transducer elements are selected for actuation or "firing" in accordance with the desired size and configuration for the ablated tissue area and/or the desired number of lesions to be contained in the ablated tissue area. The ablation device 12 is programmed via the controller to effect actuation or "firing" of the selected transducer elements when electric current or a signal is supplied to the transducer. Of course, selection and programming for actuation or "firing" of selected transducer elements can be performed prior to positioning of member 18.

Once the active face is positioned at the desired location, the power supply is activated or switched to an "on" mode to transmit electrical energy to the previously selected transducer elements. In response thereto, the piezoelectric elements corresponding to the selected transducer elements vibrate and produce ultrasound energy, which is focused within the tissue S at the corresponding focusing zones F. In the procedure of FIG. 3, all of the transducer elements are "fired" to emit ultrasound energy, causing the tissue to be heated to an ablative temperature at a focusing zone for each transducer element. The tissue S at the focusing zones is heated to a temperature in the range of 50 to 90 degrees Celsius for the time required to achieve ablation or thermal damage in the tissue. The focusing zones are contained in the target area 34. The tissue S is heated at the focusing zones to a sufficiently high temperature so as to cause a plurality of subsurface or internal lesions 38 to be simultaneously formed in the tissue S while the ultrasound emitting member 18 remains external of and does not physically penetrate the tissue S.

Lesions 38 have a generally circular surface or cross-sectional configuration as shown in FIGS. 3 and 4 and do not contact or touch one another. Lesions 38 contain ablated or damaged tissue while the tissue surrounding each lesion 38 is not heated to the ablative or thermally damaging temperature and, therefore, is unablated or undamaged. In this manner, eighteen discontinuous or non-contacting individual lesions 38 are formed in the tissue as represented in FIG. 4. Lesions 38 are contained in the internal ablated tissue area 35 coincident with the target area 34, the ablated tissue area 35 containing the lesions 38 and the unablated tissue between adjacent lesions 38. The lesions 38 have a cross-sectional length and width and a depth of known parameters depending on the size and focusing geometry of the transducer elements, the intensity of the ultrasound energy, the temperature to which the tissue is heated and the duration of ultrasound energy delivery or application to the tissue.

Due to the predetermined distance and the known length for the focusing zones, the lesions 38 and, therefore, the ablated tissue area 35, begin at the beginning or starting margin 64 located a predetermined or known depth beneath or below the external tissue surface 36 and end at the ending margin 66 located a greater predetermined or known depth beneath the external tissue surface 36, the distance between the beginning and ending margins corresponding to the depth of the lesions and, therefore, the depth of the ablated tissue area 35. By selecting the appropriate focusing zone depth and treatment parameters, a desired thickness or depth of unablated or undamaged tissue between the beginning margin 64 and the external tissue surface 36 is disposed outside the ablated tissue area. Preferably, the beginning margin is located 50 to 150 micrometers below the external tissue surface. In the method of FIGS. 3 and 4, a layer of unablated tissue about 100 micrometers thick is maintained between the external tissue surface 36 and the beginning or starting margin 64 of the lesions 38. The lesions 38 have a depth of 50 to 150 micrometers and, preferably, a depth of about 100 micrometers, in the direction perpendicular to tissue surface 36 such that the ablated tissue area and the lesions terminate or end at the ending margin 66 disposed a depth of about 200 micrometers beneath the external tissue surface 36 at the transducer/tissue interface. Accordingly, there is a perpendicular distance of about 200 micrometers from the external tissue surface to the ending margin of the ablated tissue area.

By selecting the appropriate focusing zone length and treatment parameters, the depth of the ending margin 66 within the tissue is controlled.

As shown in FIG. 4, the ablated tissue area 35, which is surrounded above, below and perimetrically by unablated or undamaged tissue, has a surface or cross-sectional configuration or area of generally rectangular shape with a cross-sectional width and length varying from 3 mm to 50 mm in either dimension, i.e. 3 mm×3 mm to 50 mm×50 mm or in between, depending on the size of the area to be treated. Although the cross-sectional length and width or other external dimensions of the ablated tissue area can be determined by the locations of the "fired" transducer elements, it should be appreciated that the cross-sectional length and/or width of the ablated tissue area can alternatively be obtained by moving the member 18 along the tissue as described in U.S. patent application Ser. No. 09/487,705, the disclosure of which is incorporated herein by reference.

Depending on the desired lesion size and/or thermal effect, ultrasound energy may be delivered or applied to the tissue for a duration in the range of 2 to 60 seconds. The emission of ultrasound energy by ultrasound emitting member 18 is terminated by the surgeon or other operator once lesions of desired size or a desired amount of tissue ablation has been obtained, and the member 18 is removed. In order to terminate the emission of ultrasound energy by the ultrasound emitting member, the power supply is deactivated or switched to an "off" mode so that electrical current is no longer supplied to the selected piezoelectric elements.

Figure 5:
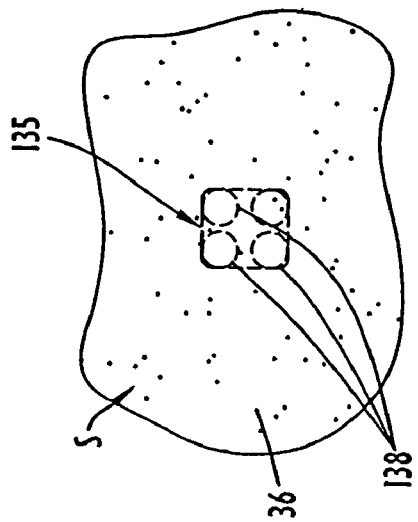
FIG. 5 is a broken top view illustrating the surface or cross-sectional configuration of an alternative ablated tissue area created in the tissue.

FIG. 5 is representative of a single treatment procedure in accordance with the present invention wherein a subsurface ablated tissue area 135 containing four non-contacting lesions 138 is formed. The ablated tissue area 135 is similar to ablated tissue area 35 except that it is of generally square surface or cross-sectional configuration or area and contains four generally circular lesions 138 each surrounded by unablated tissue. The ablated tissue area 135 can be formed using the ultrasound emitting member 18 by selecting and "firing" transducer elements R1C1, R1C2, R2C1 and R2C2, for example, to emit ultrasound energy. As described for the procedure illustrated in FIGS. 3 and 4, the ultrasound energy emitted by the selectively "fired" or actuated transducer elements is focused in the tissue at a focusing zone for each actuated transducer element, causing subsurface lesions 138 to be formed in the tissue at the focusing zones corresponding to transducer elements R1C1, R1C2, R2C1 and R2C2. The lesions 138 are similar to lesions 38 but are larger in diametric cross-sectional size than lesions 38. The ablated tissue area 135 is surrounded by unablated tissue above, below and perimetrically.

Figure 6:
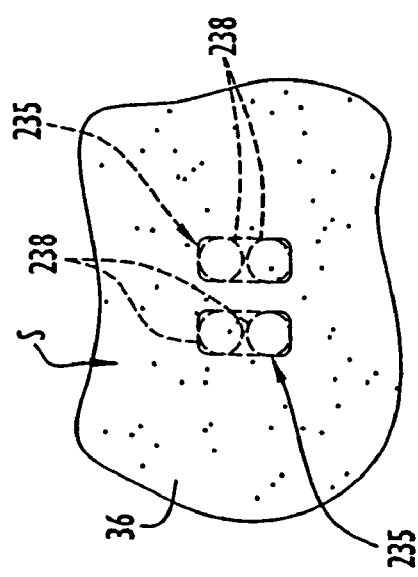
FIG. 6 is a broken top view illustrating the surface or cross-sectional configuration of a plurality of further alternative ablated tissue areas created in the tissue.

FIG. 6 is representative of a multiple treatment procedure in accordance with the present invention wherein a plurality of internal ablated tissue areas 235, each containing unablated tissue and a plurality of lesions 238, are formed or created in the tissue S. The ablated tissue areas 235 are spaced from one another, and each contains two generally circular lesions 238 similar to lesions 138 except that lesions 238 have a slightly larger cross-sectional diameter than lesions 138. The lesions 238 of each ablated tissue area 235 are spaced slightly from one another and are surrounded by unablated tissue so as to be non-contacting. Each ablated tissue area 235 has a surface or cross-sectional configuration or area of generally rectangular shape. The ablated tissue areas 235, which are similar to ablated tissue area 35 except for their cross-sectional configuration, can be formed using member 18 as described above by actuating an appropriate pair of transducer elements. The ablated tissue areas 235 are typically formed in separate treatments performed at different times. However, it should be appreciated that a plurality of ablated tissue areas, such as ablated tissue areas 235, can be formed in the tissue during a single procedure performed at one time.

FIG. 7 illustrates in dotted lines an ablated tissue area 335 of rectangular cross-sectional configuration formed in the tissue S and containing six generally circular non-contacting lesions 338 each surrounded by unablated tissue. The lesions 338 and ablated tissue area 335 are similar to the lesions 38 and ablated tissue area 35 except for the cross-sectional size of lesions 338 being different from the cross-sectional size of lesions 38. The ablated tissue area 335 will typically be formed in a single treatment or procedure. The ablated tissue area 335 can be formed using the ultrasound emitting member 18 by actuating six appropriate transducer elements.

Figure 8:
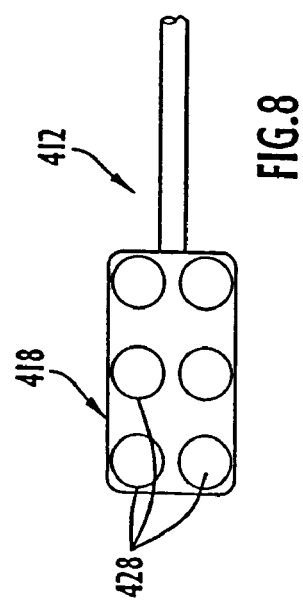
FIG. 8 is a broken bottom view of an alternative focused ultrasound ablation device having a modified ultrasound emitting member for use in the methods of the present invention.

It should be appreciated that the methods of tissue ablation according to the present invention can be performed using focused ultrasound ablation devices wherein the transducer elements of the ultrasound emitting members are not selectively actuatable. For example, FIG. 8 illustrates an alternative focused ultrasound ablation device 412 having focused ultrasound emitting member 418, which is similar to focused ultrasound emitting member 18 except that focused ultrasound emitting member 418 includes an array of six transducer elements 428 actuatable simultaneously or in unison to emit ultrasound energy. The transducer elements 428 are arranged in two rows and three columns and are used to form an ablated tissue area containing six lesions, such as ablated tissue area 335. Accordingly, it should be appreciated that various dedicated ultrasound emitting members having different arrays and/or numbers of transducer elements can be provided, with a particular ultrasound emitting member being capable of obtaining a particular ablated tissue area of predetermined size, configuration and number of lesions in response to actuation of all of the transducer elements of the particular ultrasound emitting member.

Figure 9:
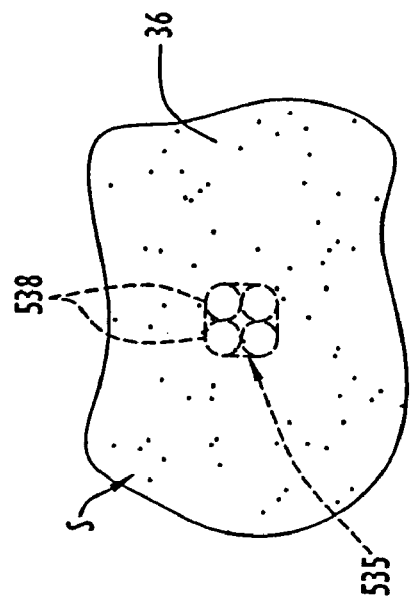
FIG. 9 is a broken top view illustrating the surface or cross-sectional configuration of an additional alternative ablated tissue area formed in the tissue.

FIG. 9 illustrates an alternative, subsurface ablated tissue area 535 formed in the tissue S in a manner similar to ablated tissue area 135. However, the ultrasound energy used to form ablated tissue area 535 is of higher intensity and/or is applied to the tissue for a longer duration than the ultrasound energy used to form ablated tissue area 135. Accordingly, the lesions 538 of ablated tissue area 535 have a generally circular surface or cross-sectional configuration larger in diameter than the generally circular cross-sectional configuration of lesions 138 due to greater dispersal of heat from the focusing zones. As a result, the lesions 538 contact or touch one another but still do not merge sufficiently to fill the entire ablated tissue area 535 with ablated tissue. Although each lesion 538 is not completely surrounded perimetrically by unablated tissue, there is still some unablated tissue within the ablated tissue area 535 as shown in FIG. 9 by unablated tissue disposed between adjacent lesions 538. It should be appreciated, therefore, that the ablated tissue areas formed in accordance with the present invention can include a plurality of non-contacting lesions each completely surrounded by unablated tissue and/or a plurality of contacting lesions with unablated tissue between the contacting lesions.

In the procedures described and illustrated above, the ultrasound emitting member is placed against the tissue at a desired location to form an ablated tissue area of final size and configuration in the tissue with focused ultrasound energy generated and emitted by the ultrasound emitting member without moving the ultrasound emitting member from the desired location. It should be appreciated, however, that where the largest size ablated tissue area capable of being formed in the tissue with the ultrasound emitting member is smaller than the final size and/or different from the final configuration desired for the ablated tissue area, the ultrasound emitting member can be moved along to form an ablated tissue area of desired final size and configuration as explained in U.S. patent application Ser. No. 09/487,705.

The methods of the present invention allow tissue ablation to be performed with minimal trauma and pain for the patient and with faster healing and recovery times. By controlling the delivery of ultrasound energy to the tissue, the temperature to which the tissue is heated by the ultrasound energy can be controlled to avoid undesired patient responses. The ultrasound emitting members can be provided with sensors for monitoring the amount of ultrasound energy delivered to the tissue and/or for detecting the temperature to which the tissue is heated, which can be provided as feedback to the controller. The delivery of ultrasound energy to tissue can be controlled to achieve a selected temperature, a selected amount of ablation, a desired lesion size or a desired duration of ultrasonic energy delivery. The transducer assembly can contain ultrasound imaging transducers that can be used to provide a real-time or multiplexed echo feedback on the progress of the ablation, in particular, the changes in mechanical properties of the tissue that are observed in eco imaging. This imaging can also be used to guide the steering and focus depth of the transducers energy focus to ensure that the desired target tissue is indeed being ablated. Furthermore, the ultrasound transducer may sense reflections from the targeted tissue such as backscatter echo and spatial compound imaging, etc. to estimate the thermal dose, tissue temperature and/or necrosis. The ultrasound emitting members can be disposable or can be designed to be reusable and thusly can be capable of being sterilized to medical standards. The ultrasound emitting members can be provided with disposable covers or guards which can be removed and discarded after use so that the ultrasound emitting members can be reused. The transducer or transducer elements can be removable from the ultrasound emitting members allowing disposability of the ultrasound emitting members and reuse of the transducer or transducer elements in another ultrasound emitting member. The ultrasound emitting members can be immobilized during use as may be accomplished with various types of stabilizing members provided on the shafts or on the ultrasound emitting members. The focused ultrasound ablation devices can be provided with imaging capabilities or can be used with various imaging devices as disclosed in U.S. patent application Ser. No. 09/487,705. The focused ultrasound ablation devices can be provided with cooling systems for cooling the ultrasound emitting members and/or the transducers as disclosed in U.S. patent application Ser. No. 09/487,705. The methods of tissue ablation can be performed using an acoustic coupling medium as disclosed in U.S. patent application Ser. No. 09/487,705. A single ultrasound emitting member can be used to form various different ablated tissue areas of various sizes, configurations, and number of lesions depending on the particular transducer elements selected for actuation. A plurality of different ultrasound emitting members having non-selectively actuatable transducer elements can be provided with each ultrasound emitting member having a different array and/or number of transducer elements to obtain a particular ablated tissue area of predetermined size, configuration and number of lesions when all of the transducer elements of the ultrasound emitting members are actuated. Any number of ablated tissue areas can be formed with each ablated tissue area surrounded by unablated tissue or with the ablated tissue areas contiguous to, in abutment with, contacting or overlapping one another to form a single ablated tissue area. The ultrasound emitting members, the transducers and/ or the transducer elements can be moved relative to the tissue to scan target areas with focused ultrasound energy, and such scanning can be accomplished in various diverse ways. The ablated tissue areas can include unablated tissue and a plurality of non-contacting lesions, a plurality of contacting lesions or a combination of contacting and non-contacting lesions. Any number of lesions can be contained in the ablated tissue areas including even and odd numbers of lesions.

In one embodiment of the present invention, a hand-held probe having one or more HIFU transducers may be used to create epicardial lesions, for example, by dragging the device across the epicardial surface of the heart. In an alternative embodiment of the present invention, a trans-esophageal ablation device having one or more HIFU transducers may be used to create tissue lesions, for example, by placing the device in a patient's esophagus and ablating cardiac tissue. In another alternative embodiment of the present invention, a trans-tracheal ablation device having one or more HIFU transducers may be used to create tissue lesions, for example, by placing the device in a patient's trachea.

Figure 10:
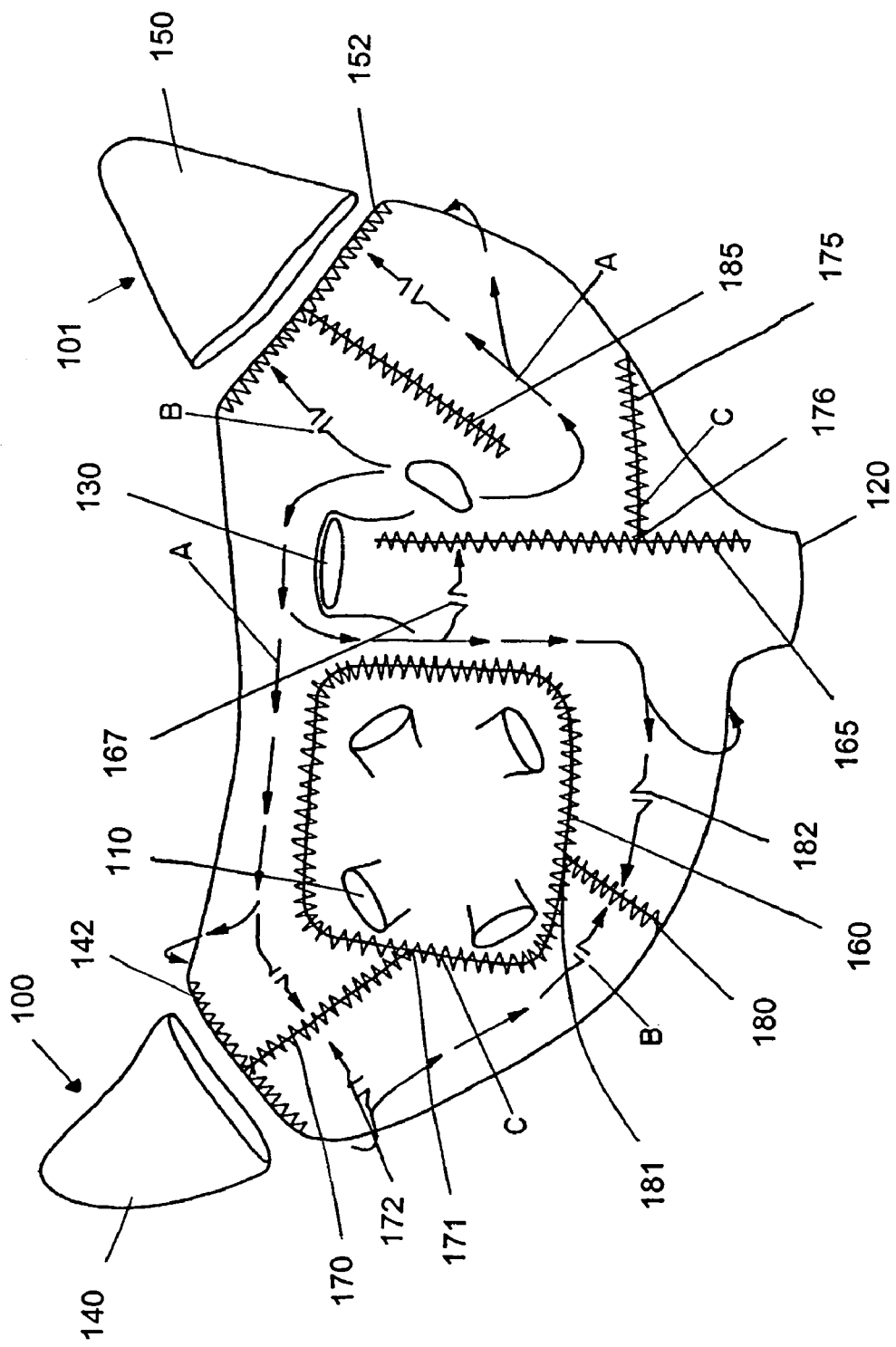
FIG. 10 shows a schematic picture of various transmural lesions of a Maze procedure which can be made with the instrument according to the invention, and which can block electrical impulses in directions crosswise to said lesions.

FIG. 10 shows diagrammatically a two-dimensional view of the two atria of a human heart, in which transmural lesions of a Maze procedure are indicated by reference letter C, the undisturbed electrical impulses by A, and the blocked electrical impulses by B. The lesions C are in the nature of scar tissue. One or more lesions C may be formed during an ablation procedure. The atria, as viewed epicardially from a lower aspect, include the left atrium 100 and the right atrium 101. Structural features of the atria include the bases of the pulmonary veins 110, the inferior vena cava 120, the superior vena cava 130, the left atrial appendage 140 and the right atrial appendage 150. A first lesion 160 is a curved lesion that is joined end-to-end such that it encircles the pulmonary veins 110, and is between the pulmonary veins 110 and conductive pathways in the left atrium 100 and between the pulmonary veins 110 and conductive pathways in the right atrium 101. A second lesion 165 extends between the superior vena cava 130 and the inferior vena cava 120 and blocks a first conductive pathway 167. A third lesion 170 extends across the left atrium 100 from an intersection 171 with a portion of the first lesion 160 toward the left atrial appendage 140 and blocks a second conductive pathway 172. A fourth lesion 175 extends along the right atrium 101 laterally from an intersection 176 with a portion of the second lesion 165 to the annulus of the tricuspid valve (not shown). A fifth lesion 180 extends from an intersection 181 with a portion of the first lesion 160 along the left atrium 100 to the annulus of the mitral valve (not shown) and blocks a third conductive pathway 182. A sixth lesion 185 extends along the right atrium 101 toward the right atrial appendage 150. Incisions 142 and 152 correspond to where the atrial appendages may be excised. Sutures may be used to close the incisions 142 and 152. Alternatively, incisions 142 and 152, or portions thereof, may be ablation lesions. One or more of the lesions discussed above may be created according to one or more embodiments of the present invention. For further details regarding the lesion pattern shown in FIG. 10, see U.S. Pat. No. 6,165,174, the disclosure of which is incorporated herein by reference. In addition, U.S. Pat. No. 6,807,968, the disclosure of which is incorporated herein by reference, also discloses the lesion pattern of a Maze ablation procedure.

In one embodiment of the present invention, ablation device 12 may be used to create a right atrial flutter lesion that extends from the tricuspid valve to the coronary sinus. In another embodiment of the present invention, ablation device 12 may be used to ablate the SA and/or AV nodes. In another embodiment of the present invention, ablation device 12 may be used to form the Wolf-Parkinson-White ablation procedure. In another embodiment of the present invention, ablation device 12 may be used to isolate the four pulmonary veins by forming a single lesion encircling of all four veins (as shown in FIG. 10). Alternatively, ablation device 12 may be used to isolate a first pair of pulmonary veins by forming a lesion encircling two of the four veins. In addition, ablation device 12 may be used to isolate the second pair of pulmonary veins by forming a lesion encircling the remaining two veins. The two encircling lesions may then be connected with a connecting lesion placed in between the two lesions, which connect the two encircling lesions together. In another embodiment of the present invention, ablation device 12 may be used to isolate each pulmonary vein individually by forming four separate lesions encircling each of the four veins. Connecting lesions may also be formed connecting the four separate lesions together, if desired.

Figure 11:
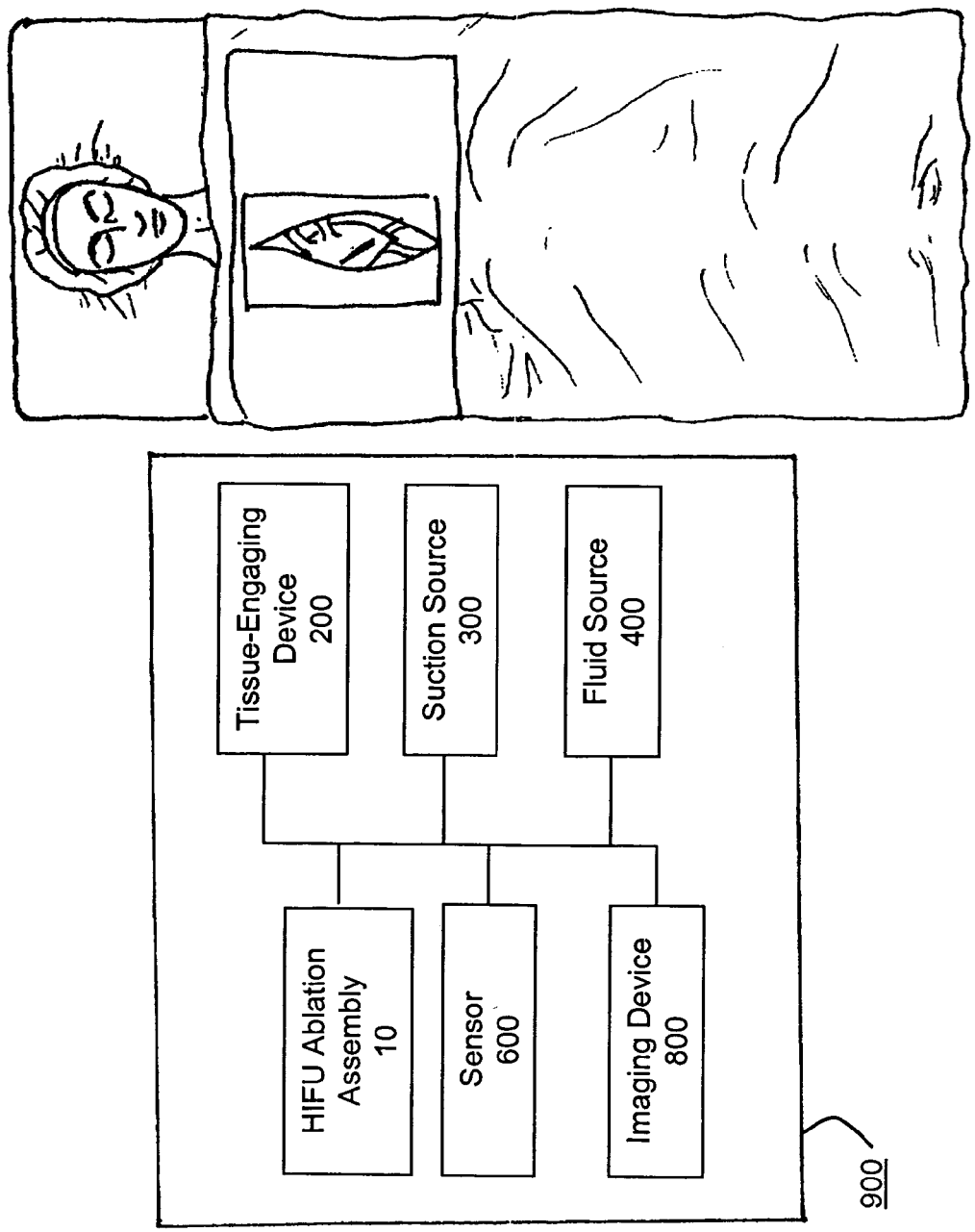
FIG. 11 is a schematic view of one embodiment of a system in accordance with the present invention.

FIG. 11 shows a schematic view of one embodiment of a system 900 for ablating tissue while positioning, manipulating, holding, grasping, immobilizing and/or stabilizing tissue in accordance with the present invention. In this embodiment, system 900 is shown to comprise tissue-engaging device 200, a suction source 300, a fluid source 400, a HIFU ablation assembly 10, a sensor 600 and an imaging device 800. The HIFU ablation assembly 10 includes a focused ultrasound ablation or stimulation device 12, a power supply 14 and a controller 16. System 900 may also include a drug delivery device, a guidance device and/or a nerve and/or cardiac stimulation device (all not shown in FIG. 11). The tissue-engaging device may comprise one or more suction or vacuum ports, openings, orifices, channels or elements positioned on, along, within or adjacent a tissue contact surface. The suction ports, openings, orifices, channels or elements may communicate suction through the tissue contact surface to the atmosphere to engage or grasp tissue via suction. The drug delivery device may be used to deliver drugs and/or biological agents to a patient. The imaging device may be used to illuminate a surgical site. The imaging and guidance devices may be used to help control and guide the HIFU device.

In one embodiment of the present invention, the tissue-engaging device may comprise one or more mechanical means for engaging and/or grasping tissue. For example, the tissue-engaging head may comprise one or more hooks, clamps, screws, barbs, sutures, straps, tethers and/or staples. The tissue-engaging device may comprise a cuff or basket-type device designed to fit completely or partially around an organ, e.g., a heart. The tissue-engaging device may comprise one or more chemical means for engaging and/or grasping tissue. For example, the tissue-engaging device may comprise tissue glue or adhesive. The tissue-engaging device may comprise one or more coupling means for engaging and/or grasping tissue. For example, a suction means in addition to a mechanical means may be used to engage or grasp tissue. A magnetic means may also be used to engage or grasp tissue.

In one embodiment of the present invention, the tissue-engaging device may include a sufficiently resiliently flexible head that may be flexed to allow it to be pushed through a small incision, cannula or port. Once inside the chest cavity, the flexible head will return to its original shape. For example, the head may be configured to be collapsable for entering into a thoracic cavity through a small incision, cannula or port in endoscopic and/or closed chest surgery. In addition, to closed chest surgery, this invention is applicable to open chest/split sternum surgery, in particular open chest, beating heart surgery for repositioning the heart to improve access to various locations of the heart.

The tissue-engaging device may include one or more fluid openings for delivery and/or removal of one or more fluids. The tissue-engaging device may include needles for injection of fluids, drugs and/or cells into organ tissue. The tissue-engaging device may comprise a catheter or cannula for blood removal or delivery into an organ, e.g., a heart. In the case of the heart, the cannula or catheter may be placed through the wall of the heart and into an interior chamber of the heart comprising blood, for example, into the left ventricle. Blood may be removed or delivered via a blood pump. For example, a catheter or cannula of the tissue-engaging device may be attached to a CPB circuit or a cardiac assist circuit such as an LVAD circuit. The tissue-engaging device may include one or more openings for delivery or removal of one or more gases including smoke evacuation.

One or more parts or portions of the tissue-engaging device may be designed to be implantable. For example, following an ablation procedure, a head portion of the tissue-engaging device may be left within the patient, thereby providing benefit to the patient. The tissue-engaging head may be made of one or more biodegradable materials, thereby allowing the head to be absorbed by the patient over time.

The tissue-engaging device may comprise a maneuvering or support apparatus or means such as a shaft, a handle or an arm connected to a tissue-engaging head to position the head to thereby position or hold tissue such as the heart. The tissue-engaging head of the tissue-engaging device may be rigidly, permanently, moveably, or removeably coupled, connected or mounted onto the maneuvering or support apparatus or means. The support shaft, handle or arm may be rigid, flexible, telescoping or articulating. The shaft, handle or arm may comprise one or more hinges or joints for maneuvering and placing the device against tissue. The hinges or joints of the maneuvering or support apparatus may be actuated remotely, for example with pull wires, from outside a patient's body. The shaft, handle or arm may be malleable or shapeable. The maneuvering or support means may be made of a shape memory alloy wherein heat may be use to change the shape of the maneuvering or supporting means.

In one method of the present invention, the medical procedure may include the use of a tissue-engaging device as described, for example, in U.S. patent application Ser. No. 10/643,299, U.S. Patent Application Publication No. 2004/0138522 and U.S. Pat. No. 6,447,443, the disclosures of which are incorporated herein by reference, in combination with one or more focused ultrasound ablation devices. The combination of one or more tissue-engaging devices and one or more tissue ablation devices may be used to position and ablate tissue, e.g., endocardial, myocardial and/or epicardial tissue of the heart, located within a body cavity, e.g.,.the thoracic cavity. Other body organ tissue, such as the liver, lungs or kidney, may also be positioned and ablated. An ablation procedure that utilizes a tissue-engaging device may be an open chest procedure, a closed chest procedure, a minimally invasive procedure, a beating heart procedure, and/or a stopped heart procedure. The tissue-engaging device may be positioned and used, for example, through a sternotomy, through a thoracotomy that avoids the sternal splitting incision of conventional cardiac surgery, through a mini-thoracotomy, through a sub-xyphoid incision, percutaneously, transvenously, arthroscopically, endoscopically, for example, through a percutaneous port, through a stab wound or puncture, through a small or large incision, for example, in the chest, in the groin, in the abdomen, in the neck or in the knee, or in combinations thereof. The tissue-engaging device may be guided into a desired position using various imaging and/or guidance techniques, e.g., fluoroscopic guidance techniques.

Tissue-engaging device 200 may be used to grasp and position the pericardium away from the surface of the heart thereby creating space between the surface of the heart and the pericardium. This type of procedure may be termed "tenting". Tissue-engaging device 200 may be used to grasp and position a heart away from a rib cage, for example in an endoscopic procedure, thereby creating space for a surgeon to work between the heart and the rib cage. Tissue-engaging device 200 may be used to grasp and position a heart away from other adjacent or nearby organs thereby creating space for a surgeon to work.

An endoscope or thoracoscope may be used to view on or more aspects of the medical procedure. Incisions may be maintained open by insertion of a cannula or port through the incision so that instruments, such as a tissue-engaging device and/or HIFU ablation device, can be advanced through the lumen of the cannula or port. If a trocar is used, a trocar rod is inserted into the trocar sleeve, and the sharpened tip of the trocar rod is advanced to puncture the abdomen or chest to create the incision into the thoracic cavity. The trocar rod is then withdrawn leaving the trocar sleeve in place so that one or more surgical instruments may be inserted into the thoracic cavity through the trocar sleeve lumen.

In one embodiment of the invention, the surgeon may decide to stop the heart. For example, a series of catheters may be used to stop blood flow through the aorta and to administer cardioplegia solution. A closed chest, stopped heart procedure may utilize groin cannulation to establish cardiopulmonary bypass (CPB) and an intra-aortic balloon catheter that functions as an internal aortic clamp by means of an expandable balloon at its distal end used to occlude blood flow in the ascending aorta. A full description of one example of an endoscopic technique is found in U.S. Pat. No. 5,452,733, the disclosure of which is incorporated herein by reference.

Figure 12:
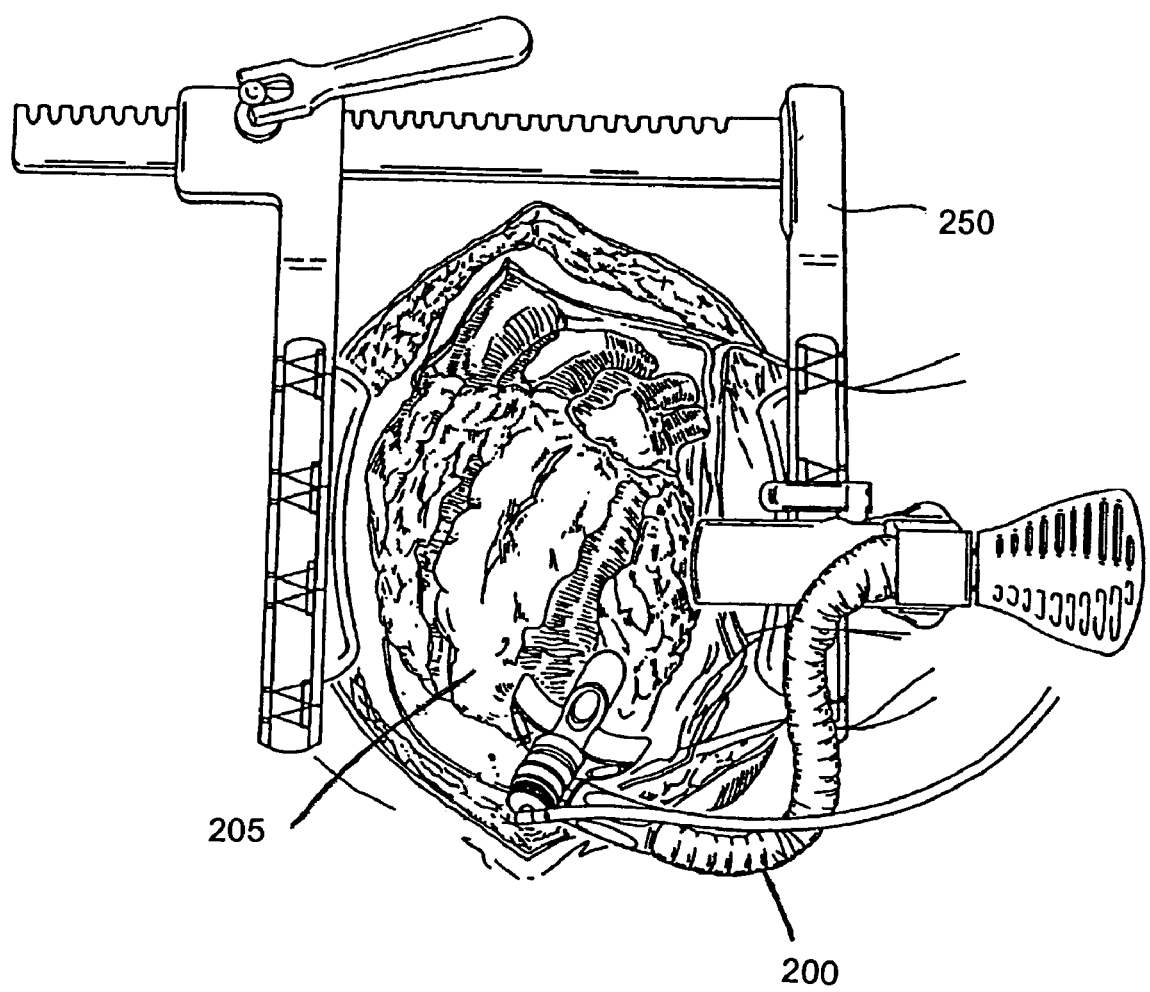
FIG. 12 is an illustration of one embodiment of a medical device in use in accordance with the present invention.
Figure 13:
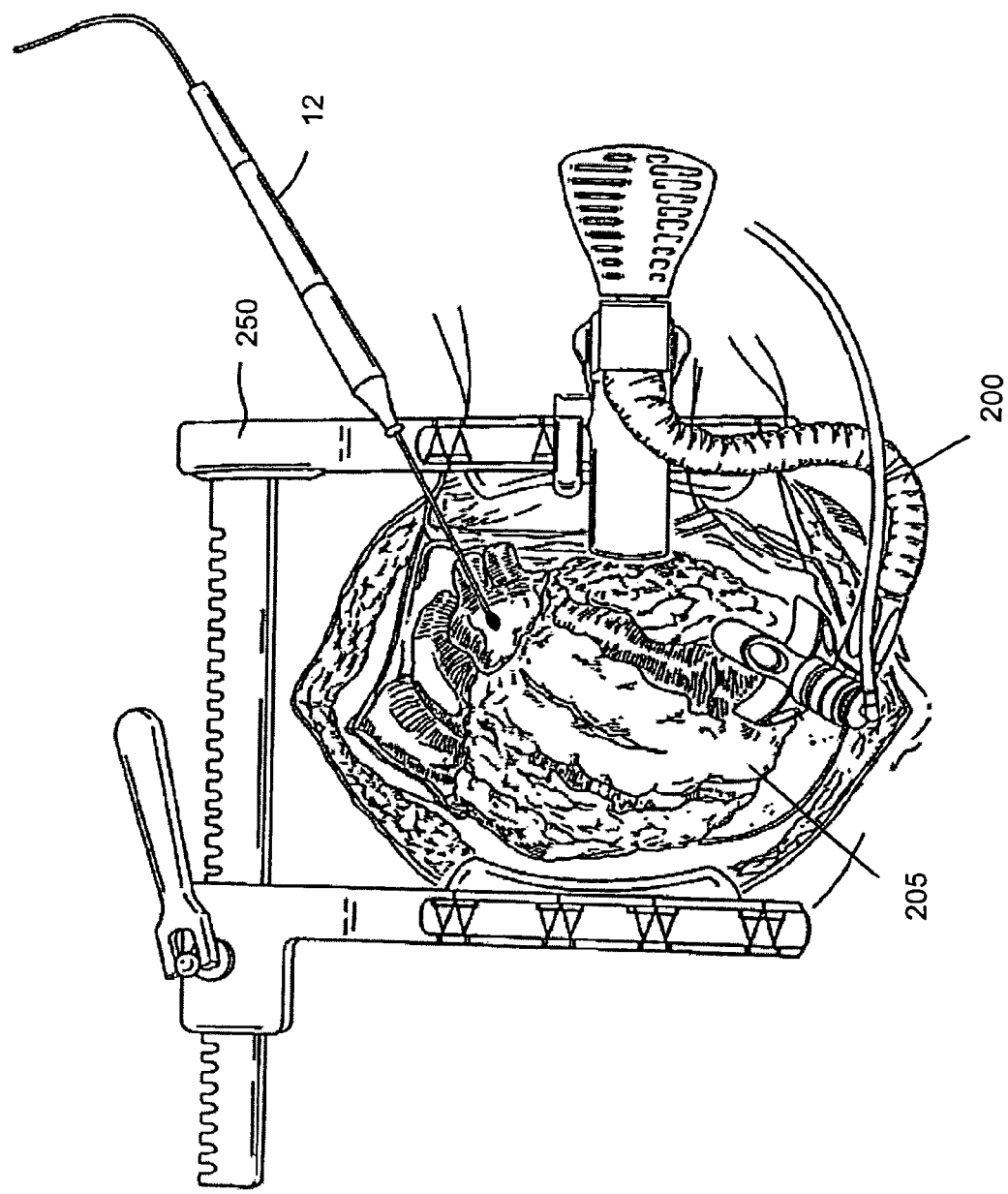
FIG. 13 is an illustration of one embodiment of a medical device in use in accordance with the present invention.

The tissue-engaging device may be used to position, manipulate, hold, grasp, immobilize and/or stabilize an area of tissue and/or an organ, such as a heart, during an ablation procedure. For example, the tissue-engaging device may be used to engage an area of tissue, such as an organ, and position the area of tissue or organ into a non-physiological orientation. For example, the tissue-engaging device 200, shown in FIG. 12, is shown being used in an open chest, sternotomy procedure to position the heart into a non-physiological orientation, thereby creating access to areas of the heart that an ablation device positioned, for example, through the chest opening or sternotomy would not have had ablative access to prior to positioning of the heart. FIG. 12 shows tissue-engaging device 200 locked onto a sternal retractor 250 fixed to a patient's chest. In FIG. 12, tissue-engaging device 200 is shown supporting a patient's heart 205 while it is engaged or attached to the apex of the patient's heart. The patient's heart may be beating or stopped. As shown in FIG. 13, a hand-held ablation device 12 positioned through a sternotomy and having at least one HIFU transducer may be used to create one or more epicardial lesions, for example, by moving or dragging the device across the epicardial surface of the heart. As shown in FIG. 13, the one or more epicardial lesions may be made while the heart is positioned in a non-physiological orientation.

Figure 14:
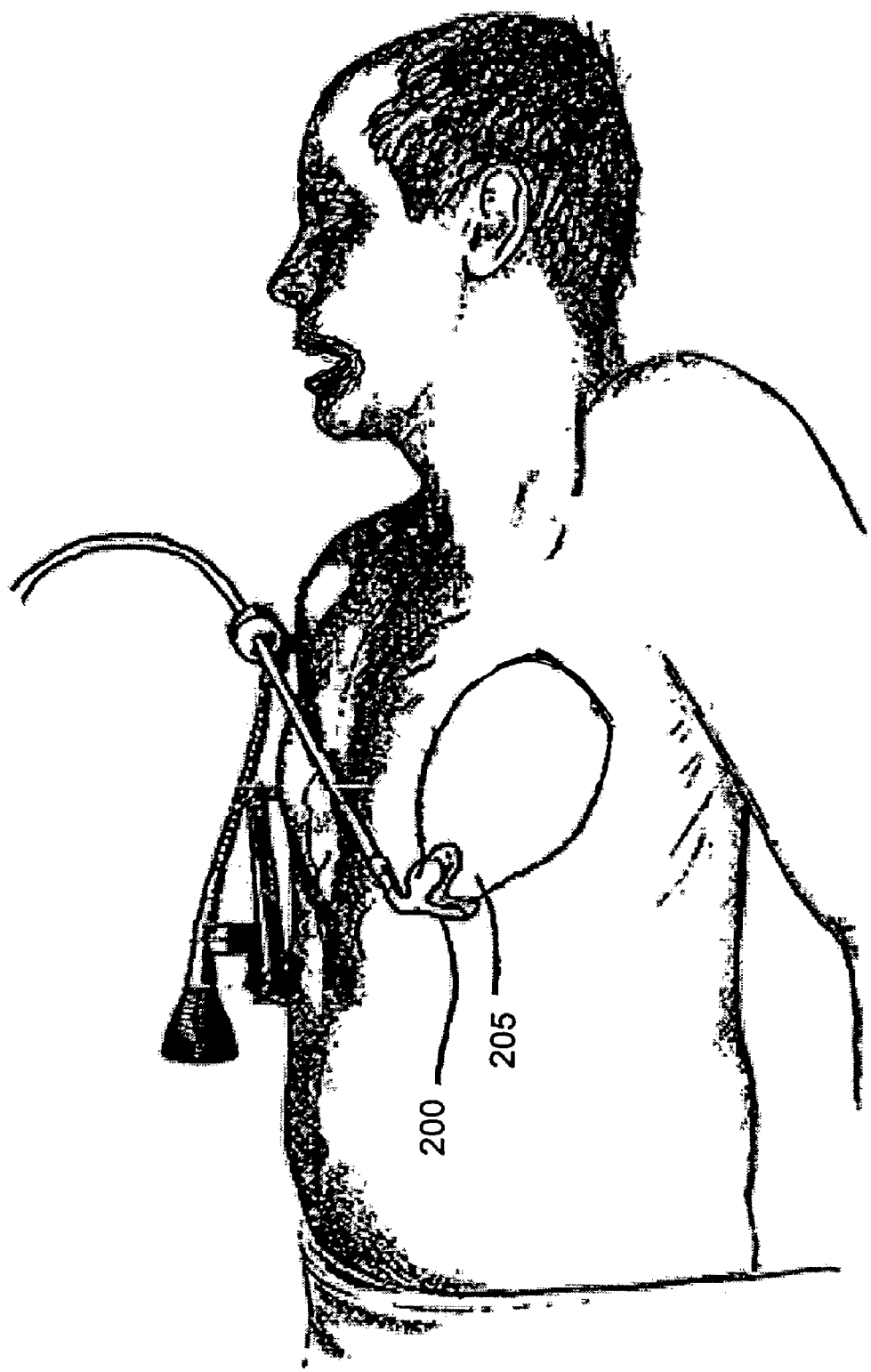
FIG. 14 is an illustration of one embodiment of a medical device in use in accordance with the present invention.

The tissue-engaging device 200, shown in FIG. 14, is shown being used in a closed chest, non-sternotomy procedure to position the heart 205 into a non-physiological orientation. Positioning the heart in a non-physiological can create access to areas of the heart that an ablation device positioned, for example, through a thoracotomy or port, through the patient's esophagus or trachea, or positioned outside the chest would not have had ablative access to prior to positioning of the heart.

In one method of the present invention, a focused ultrasound ablation device 12 is placed within the trachea and/or bronchi of the lungs to ablate tissue within the thoracic cavity of a patient. The ultrasound ablation device is sized and shaped to fit within the trachea and/or bronchi of the lungs. Shaft 20 may be of a sufficient length to allow insertion of an appropriately sized ultrasound emitting member 18 into the trachea and/or bronchi of the lungs of a patient through the patient's oral cavity. Once placed in the desired position, ultrasound energy may be focused through the wall of the trachea or bronchi and into tissue to be ablated. To ablate tissue not positioned within the focusing range of the ultrasound ablation device, a tissue-engaging device, as described earlier, may be used to move and position tissue of interest within the focusing range of the ablation device. The tissue-engaging device may be used to position tissue prior to an ablation procedure, during an ablation procedure and/or following an ablation procedure. A variety of tissue types and/or organs may be ablated or treated by one or more ultrasound ablations device placed within the trachea and/or bronchi of the lungs. Alternatively, a variety of tissue types and/or organs may be ablated or treated by one or more ultrasound ablation devices positioned through one or more other body cavity openings of the patient and/or positioned on the skin of the patient. For example, one or more ultrasound ablation devices may be positioned through the mouth, the nose, the anus, the urethra and/or the vagina. The ablation procedure may include one or more imaging methods or devices.

Figure 15:
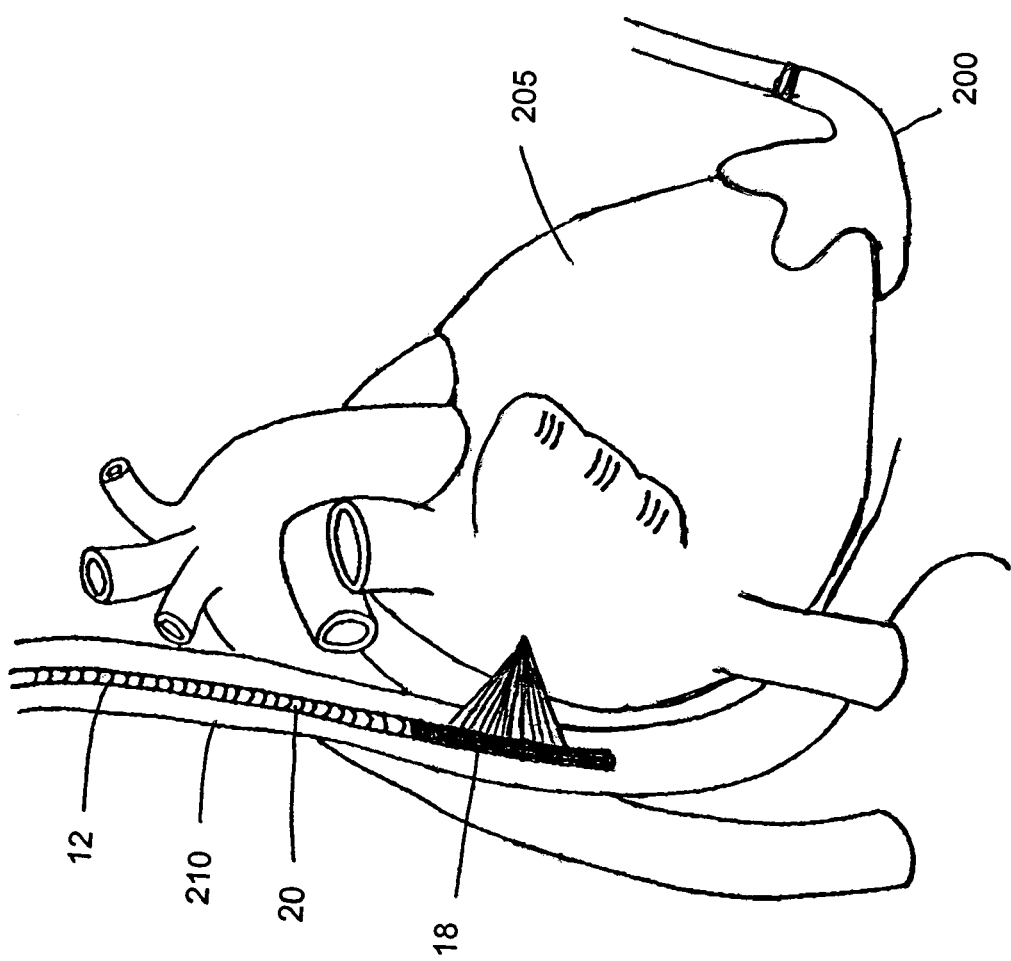
FIG. 15 is an illustration of one embodiment of a medical device in use in accordance with the present invention.

In one method of the present invention, see FIG. 15, a focused ultrasound ablation device 12 is placed within the esophagus 210 to ablate tissue of the heart 205, for example, in a Maze procedure. The ultrasound ablation device may be sized and shaped to fit within the esophagus 210. Shaft 20 may be of a sufficient length to allow insertion of an appropriately sized ultrasound emitting member 18 into the esophagus of a patient through the patient's oral cavity. Once placed in the desired position, ultrasound energy may be focused through the wall of the esophagus and into cardiac tissue to be ablated. Cardiac tissue is then ablated. To ablate cardiac tissue not positioned within the focusing range of the ultrasound ablation device, a tissue-engaging device 200, as described earlier, may be used to move and position the heart to move tissue of interest within the focusing range of the ablation device. The tissue-engaging device 200 may be used to position tissue prior to an ablation procedure, during an ablation procedure and/or following an ablation procedure. In addition to cardiac tissue, other tissue types and/or organs may be ablated or treated by one or more ultrasound ablation devices placed within the esophagus of the patient.

In one embodiment of the invention, ablation device 12 may comprise, for example, one or more inflatable and/or compressible members, which may be inflated or decompressed with air or liquid, for example, while the device is positioned within a body cavity to press the surface of the ablating member 18 firmly against the body cavity wall. For example, device 12 may comprise a balloon, which may be inflated with air or liquid while the device is positioned within the esophagus, the trachea and/or bronchi of the lungs to press the surface of the ablating member 18 firmly against the body cavity wall.

Figure 16:
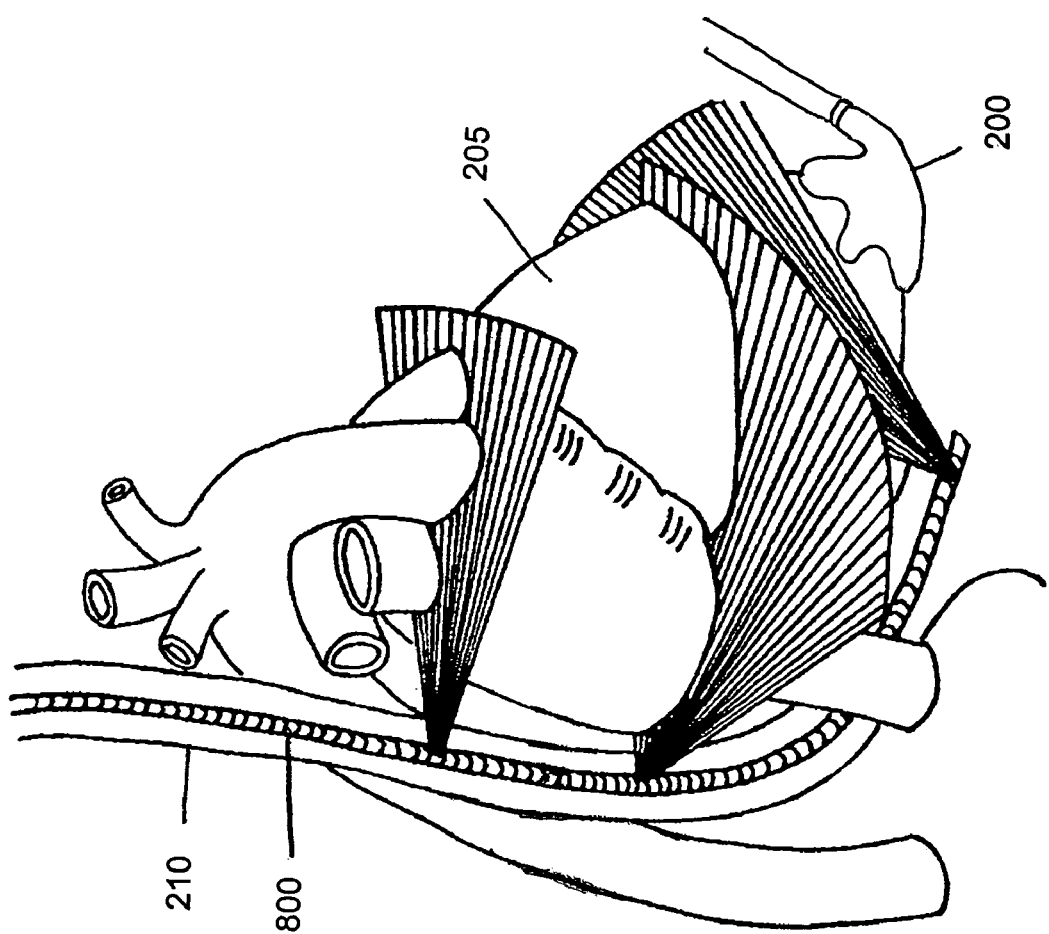
FIG. 16 is an illustration of one embodiment of a medical device in use in accordance with the present invention.

In one method of the present invention, an imaging device 800 may be used to image tissue such as heart tissue as shown in FIG. 16. The imaging device may be appropriately sized to allow its placement within the esophagus of the patient. Alternatively, the imaging device may be appropriately sized to allow its placement within the trachea and/or bronchi of the lungs of the patient. Alternatively, one or more imaging devices may be positioned through one or more other body cavity openings of the patient and/or positioned on the skin of the patient. For example, one or more imaging devices may be positioned through the mouth, the nose, the anus, the urethra and/or the vagina. In one embodiment of the present invention, ablation system 10 may include one or more imaging capabilities. For example, ultrasound imaging capabilities may be incorporated into ultrasound ablation device 12 so that a single device could be used to both image and ablate tissue. Once placed in the desired position, for example in the esophagus, ultrasound energy may be focused through the wall of the esophagus and into cardiac tissue to be imaged. Cardiac tissue is then imaged and the location of tissue to be ablated is determined. To image cardiac tissue not positioned within the focusing range of the imaging device, a tissue-engaging device 200, as described earlier, may be used to move and position the tissue of interest within the focusing range of the imaging device. The tissue-engaging device 200 may be used to position tissue prior to an imaging procedure, during an imaging procedure and/or following an imaging procedure. In addition to cardiac tissue, other tissue types and/or organs may be positioned and imaged by one or more positioning and imaging devices. In one embodiment of the present invention, the positioning or tissue-engaging device may comprise one or more imaging capabilities, e.g., ultrasound imaging.

In one embodiment of the present invention, a nerve stimulator comprising one or more nerve stimulation electrodes may be used to stimulate the patient's vagal nerve to slow or stop the patient's heart during an ablation procedure. The patient may be given one or more drugs to help stop the beating of the heart and/or to prevent "escape" beats. Following vagal stimulation, the heart may be allowed to return to its usual cardiac rhythm. Alternatively, the heart may be paced, thereby maintaining a normal cardiac output. Vagal stimulation, alone or in combination with electrical pacing and/or drugs, may be used selectively and intermittently to allow a surgeon to perform an ablation procedure on a temporarily stopped heart. For example, stimulation of the vagus nerve in order to temporarily and intermittently slow or stop the heart is described in U.S. Pat. No. 6,006,134, No. 6,449,507, No. 6,532,388, No. 6,735,471, No. 6,718,208, No. 6,228,987, No. 6,266,564, No. 6,487,446 and U.S. patent applications Ser. No. 09/670,370 filed Sep. 26, 2000, Ser. No. 09/669,961 filed Sep. 26, 2000, Ser. No. 09/670,440 filed Sep. 26, 2000. These patents and patent applications are incorporated herein by reference in their entireties.

Electrodes used to stimulate a nerve such as the vagal nerve may be, for example, non-invasive, e.g., clips, or invasive, e.g., needles or probes. The application of an electrical stimulus to the right or left vagal nerve may include, but is not limited to bipolar and/or monopolar techniques. Different electrode positions are accessible through various access openings, for example, in the cervical or thorax regions. Nerve stimulation electrodes may be positioned through a thoracotomy, sternotomy, endoscopically through a percutaneous port, through a stab wound or puncture, through a small incision in the neck or chest, through the internal jugular vein, the esophagus, the trachea, placed on the skin or in combinations thereof. Electrical stimulation may be carried out on the right vagal nerve, the left vagal nerve or to both nerves simultaneously or sequentially. The present invention may include various electrodes, catheters and electrode catheters suitable for vagal nerve stimulation to temporarily stop or slow the beating heart alone or in combination with other heart rate inhibiting agents.

Nerve stimulation electrodes may be endotracheal, endoesophageal, intravascular, transcutaneous, intracutaneous, patch-type, balloon-type, cuff-type, basket-type, umbrella-type, tape-type, screw-type, barb-type, metal, wire or suction-type electrodes. Guided or steerable catheter devices comprising electrodes may be used alone or in combination with the nerve stimulation electrodes. For example, a catheter comprising one or more wire, metal strips or metal foil electrodes or electrode arrays may be inserted into the internal jugular vein to make electrical contact with the wall of the internal jugular vein, and thus stimulate the vagal nerve adjacent to the internal jugular vein. Access to the internal jugular vein may be via, for example, the right atrium, the right atrial appendage, the inferior vena cava or the superior vena cava. The catheter may comprise, for example, a balloon, which may be inflated with air or liquid to press the electrodes firmly against the vessel wall. Similar techniques may be performed by insertion of a catheter-type device into the trachea or esophagus. Additionally, tracheal devices, e.g., tracheal tubes, tracheal ablation devices, tracheal imaging devices, and/or esophageal devices, e.g., esophageal tubes, esophageal ablation devices, esophageal imaging devices, comprising electrodes may be used.

Nerve stimulation electrodes may be oriented in any fashion along the catheter device, including longitudinally or transversely. Various imaging techniques or modalities, as discussed earlier, such as ultrasound, fluoroscopy and echocardiography may be used to facilitate positioning of the electrodes. If desired or necessary, avoidance of obstruction of air flow or blood flow may be achieved with notched catheter designs or with catheters, which incorporate one or more tunnels or passageways.

In one embodiment of the present invention, the location of the electrodes is chosen to elicit maximum bradycardia effectiveness while minimizing current spread to adjacent tissues and vessels and to prevent the induction of post stimulation tachycardia. Furthermore, a non-conductive material such as plastic may be employed to sufficiently enclose the electrodes of all the configurations to shield them from the surrounding tissues and vessels, while exposing their confronting edges and surfaces for positive contact with the vagal nerve or selected tissues.

Figure 17:
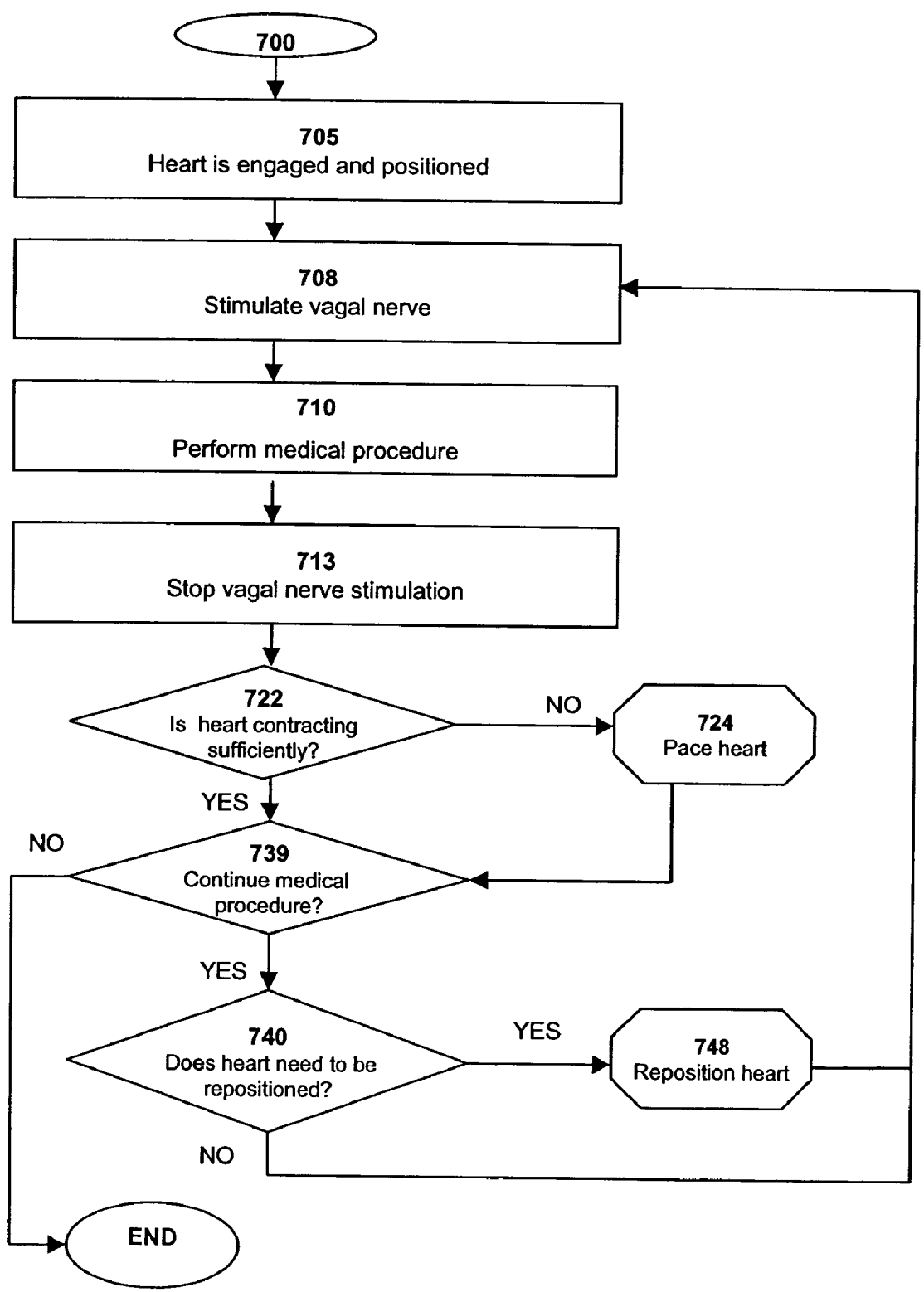
FIG. 17 is a flow diagram of one embodiment of the present invention.

FIG. 17 shows a flow diagram of one embodiment of the present invention. The patient is prepared for a medical procedure at 700. Once the patient is prepared, the heart is engaged and positioned using tissue-engaging device 200 (Block 705). Once the heart is positioned in a desired orientation, e.g., a non-physiological orientation, a nerve that controls the beating of the heart is stimulated to slow down or stop the contractions of the heart (Block 708). Such a nerve may be for example a vagal nerve. During this time, one or more of a variety of pharmacological agents or drugs may be delivered to the patient. Drugs may be administered without nerve stimulation. The types of drugs administered may produce reversible asystole of a heart while maintaining the ability of the heart to be electrically paced. Other drugs may be administered for a variety of functions and purposes. Drugs may be administered at the beginning of the procedure, intermittently during the procedure, continuously during the procedure or following the procedure. Examples of one or more drugs that may be administered include a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

Typically, vagal nerve stimulation prevents the heart from contracting. This non-contraction must then be followed by periods without vagal nerve stimulation during which the heart is allowed to contract, and blood flow is restored throughout the body. Following initial slowing or stopping of the heart, a medical procedure, such as imaging and/or ablation, is begun (Block 710). In one embodiment of the invention, one or more ultrasound ablation devices are positioned within the trachea, bronchi of the lungs and/or esophagus of the patient and ultrasound energy is emitted from the one or more ablation devices and is focused within tissue, e.g., cardiac tissue. Alternatively, an ablation device may be placed on the patient, e.g., on the chest of the patient. Following a brief interval of nerve stimulation while the ablation procedure is performed, nerve stimulation is ceased (Block 713) and the heart is allowed to contract.

The heart may be free to beat on its own or a cardiac stimulator or pacemaker comprising one or more cardiac stimulation electrodes may be used to cause the heart to contract (Blocks 722 and 724). Cardiac stimulation electrodes used to stimulate the heart may be, for example, non-invasive, e.g., clips, or invasive, e.g., needles or probes. Cardiac electrodes may be positioned through a thoracotomy, sternotomy, endoscopically through a percutaneous port, through a stab wound or puncture, through a small incision in the chest, placed on the chest or in combinations thereof. The present invention may also use various electrodes, catheters and electrode catheters suitable for pacing the heart, e.g., epicardial, patch-type, intravascular, balloon-type, basket-type, umbrella-type, tape-type electrodes, suction-type, pacing electrodes, endotracheal electrodes, endoesophageal electrodes, transcutaneous electrodes, intracutaneous electrodes, screw-type electrodes, barb-type electrodes, bipolar electrodes, monopolar electrodes, metal electrodes, wire electrodes and cuff electrodes. Guided or steerable catheter devices comprising electrodes may be used alone or in combination with the electrodes. One or more cardiac electrodes, e.g., stimulation and/or monitoring electrodes, may be positioned on tissue-engaging device 200.

If the ablation procedure needs to continue or a new ablation procedure is to be performed, the heart again may be slowed or stopped via vagal nerve stimulation. In addition, the heart may be repositioned if necessary or desired at Block 748.

In one embodiment of the present invention, a probe device sized and shaped to fit within the trachea, bronchi and/or esophagus of the patient may comprise one or more nerve stimulation electrodes, members or elements and one or more ultrasound ablation members or elements. The probe device may be positioned within the trachea, bronchi and/or esophagus of the patient. The nerve stimulation electrodes may be used to stimulate one or more nerves of the patient, e.g., a vagal nerve, as disclosed earlier, while the probe device is positioned within the trachea, bronchi and/or esophagus of the patient. The ultrasound ablation members may be used to emit ultrasound energy to ablate tissue, e.g., cardiac tissue, as disclosed earlier, while the probe device is positioned within the trachea, bronchi and/or esophagus of the patient. The nerve stimulation electrodes may be coupled to a nerve stimulator, e.g., used to stimulate the patient's vagal nerve to slow or stop the patient's heart during an ablation procedure.

In one embodiment of the present invention, the tissue-engaging device may include one or more ultrasound ablation elements, as described earlier. The tissue-engaging device comprising one or more ultrasound ablation elements may be used to move and position tissue, e.g., heart tissue, as well as to ablate tissue within the focusing range of the one or more ultrasound ablation elements. The tissue-engaging device may be used to position tissue prior to an ablation procedure, during an ablation procedure and/or following an ablation procedure. In addition to cardiac tissue, other tissue types and/or organs may be ablated or treated by one or more ultrasound ablation elements of the device.

The distal end of the tissue-engaging device may be positioned within a patient through an incision, a stab wound, a port, a sternotomy and/or a thoracotomy. An endoscope may be used to help position the tissue-engaging device.

In one embodiment of the present invention, the ultrasound ablation device or system may comprise one or more switches to facilitate its regulation by a physician or surgeon. One example of such a switch is a foot pedal. The switch may also be, for example, a hand switch, or a voice-activated switch comprising voice-recognition technologies. The switch may be incorporated in or on one of the surgeon's instruments, such as surgical site retractor, or any other location easily and quickly accessed by the surgeon.

The ultrasound ablation device or system may include a display and/or other means of indicating the status of various components of the device to the surgeon such as a numerical display, gauges, a monitor display or audio feedback. The ultrasound ablation device may also include one or more visual and/or audible signals used to prepare a surgeon for the start or stop of the ablation procedure. Controller 16 may synchronize deliver of ablation energy to the ablation device 12 between heart beats to reduce inadvertent tissue damage. Controller 16 may be slaved to a nerve stimulator and/or a cardiac stimulator. Alternatively, a nerve stimulator and/or cardiac stimulator may be slaved to controller 16. Alternatively, controller 16 may be capable of nerve stimulation and/or cardiac stimulation.

In one embodiment of the present invention, one or more diagnostic transducers may be used to measure the desired ablative tissue area. System 900 would then suggest and/or control a specific transducer based on the desired lesion depth and configuration. The system could then deliver the amount and type of energy required to create the desired lesion. Electrodes of system 900 may be used for cardiac pacing, defibrillation, cardioversion, sensing, stimulation, and/or mapping.

System 900 may include suction source 300 for providing suction to tissue-engaging device 200 and/or ablation device 12. Tissue-engaging device 200 and/or ablation device 12 may be attached to a flexible or rigid hose or tubing for supplying suction and/or fluids from a suitable suction source and/or fluid source to the target tissue surface through suction and/or fluid elements, openings, orifices, or ports of device 200 and/or device 12. The hose or tubing may comprise one or more stopcocks and/or connectors such as luer connectors. Suction may be provided to device 200 and/or device 12 by the standard suction available in the operating room. Suction source 300 may be coupled to tissue -engaging device 200 and/or device 12 with a buffer flask and/or filter. Suction may be provided at a negative pressure of between 200-600 mm Hg with 400 mm Hg preferred. As used herein, the terms "vacuum" or "suction" refer to negative pressure relative to atmospheric or environmental air pressure in the operating room.

Suction may be provided via one or more manual or electric pumps, syringes, suction or squeeze bulbs or other suction or vacuum producing means, devices or systems. Suction source 300 may comprise one or more vacuum regulators, resistors, stopcocks, connectors, valves, e.g., vacuum releasing valves, filters, conduits, lines, tubes and/or hoses. The conduits, lines, tubes, or hoses may be flexible or rigid. For example, a flexible suction line may be used to communicate suction to device 200 and/or device 12, thereby allowing device 200 and/or device 12 to be easily manipulated by a surgeon. Another method that would allow the surgeon to easily manipulate device 200 and/or device 12 includes incorporation of suction source 300 into device 200 and/or device 12. For example, a small battery operated vacuum pump or squeeze bulb may be incorporated into device 200 and/or device 12.

Suction source 300 may be slaved to ablation assembly 10, tissue-engaging device 200, fluid source 400, sensor 600, imaging device 800, a drug delivery device, a guidance device and/or a stimulation device. For example, suction source 300 may be designed to automatically stop suction when controller 16 sends a signal to stop suction. Suction source 300 may include a visual and/or audible signal used to alert a surgeon to any change in suction. For example, a beeping tone or flashing light may be used to alert the surgeon when suction is present. Suction source 300 may be slaved to a robotic system or a robotic system may be slaved to suction source 300. Suction may be used to secure, anchor or fix tissue-engaging device 200 and/or device 12 to an area of tissue. The area of tissue may comprise a beating heart or a stopped heart. Suction may be used to remove or aspirate fluids from the target tissue site. Fluids removed may include, for example, blood, saline, Ringer's solution, ionic fluids, contrast fluids, irrigating fluids and energy-conducting fluids. Steam, vapor, smoke, gases and chemicals may also be removed via suction.

System 900 may include fluid source 400 for providing fluids, for example, to tissue-engaging device 200, ablation device 12 and/or the patient. Tissue-engaging device 200 may be attached to a flexible or rigid hose or tubing for supplying fluids from fluid source 400 to the target tissue through fluid elements, openings, orifices, or ports of device 200. Ablation device 12 may be attached to a flexible or rigid hose or tubing for receiving fluids from fluid source 400 and for supplying fluids, if desired, to the target tissue through fluid elements, openings, orifices, or ports of device 12.

Fluid source 400 may be any suitable source of fluid. Fluid source 400 may include a manual or electric pump, an infusion pump, a peristaltic pump, a roller pump, a centrifugal pump, a syringe pump, a syringe, or squeeze bulb or other fluid moving means, device or system. For example, a pump may be connected to a shared power source or it may have its own source of power. Fluid source 400 may be powered by AC current, DC current, or it may be battery powered either by a disposable or re-chargeable battery. Fluid source 400 may comprise one or more fluid regulators, e.g., to control flow rate, valves, fluid reservoirs, resistors, filters, conduits, lines, tubes and/or hoses. The conduits, lines, tubes, or hoses may be flexible or rigid. For example, a flexible line may be connected to devices 12 and/or 200 to deliver fluid and/or remove fluid, thereby allowing device 200 to be easily manipulated by a surgeon. Fluid reservoirs may include an IV bag or bottle, for example.

Fluid source 400 may be incorporated into tissue-engaging device 200 and/or ablation device 12, thereby delivering fluid or removing fluid at the target tissue site. Fluid source 400 may be slaved to tissue-engaging device 200 and/or ablation device 12, suction source 300, sensor 600 and/or imaging device 800. For example, fluid source 400 may be designed to automatically stop or start the delivery of fluid while tissue-engaging device 200 is engaged with tissue or while ablation device 12 is ablating tissue. Ablation system 10, tissue-engaging device 200, suction source 300, fluid source 400, sensor 600 and/or imaging device 800 may be slaved to a robotic system or a robotic system may be slaved to ablation system 10, tissue-engaging device 200, suction source 300, fluid source 400, sensor 600 and/or imaging device 800.

Fluid source 400 may comprise one or more switches, e.g., a surgeon-controlled switch. One or more switches may be incorporated in or on fluid source 400 or any other location easily and quickly accessed by the surgeon for regulation of fluid delivery by the surgeon. A switch may be, for example, a hand switch, a foot switch, or a voice-activated switch comprising voice-recognition technologies. A switch may be physically wired to fluid source 400 or it may be a remote control switch. Fluid source 400 and/or system 10 may include a visual and/or audible signal used to alert a surgeon to any change in the delivery of fluid. For example, a beeping tone or flashing light may be used to alert the surgeon that a change has occurred in the delivery of fluid.

Fluids delivered to tissue-engaging device 200 and/or ablation device 12 may include saline, e.g., normal, hypotonic or hypertonic saline, Ringer's solution, ionic, contrast, blood, and/or energy-conducting liquids. An ionic fluid may electrically couple an electrode to tissue thereby lowering the impedance at the target tissue site. An ionic irrigating fluid may create a larger effective electrode surface. An irrigating fluid may cool the surface of tissue thereby preventing over heating or cooking of tissue which can cause popping, desiccation, and charring of tissue. A hypotonic irrigating fluid may be used to electrically insulate a region of tissue. Fluids delivered to tissue-engaging device 200 and/or ablation device 12 may include gases, adhesive agents and/or release agents.

Diagnostic or therapeutic agents, such as one or more radioactive materials and/or biological agents such as, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and a dye (which acts as a biological ligand) may be delivered with or without a fluid to the patient. Biological agents may be found in nature (naturally occurring) or may be chemically synthesized. Cells and cell components, e.g., mammalian and/or bacterial cells, may be delivered to the patient. A platelet gel or tissue adhesive may be delivered to the patient.

One or more of a variety of pharmacological agents, biological agents and/or drugs may be delivered or administered to a patient, for a variety of functions and purposes as described below, prior to a medical procedure, intermittently during a medical procedure, continuously during a medical procedure and/or following a medical procedure. For example, one or more of a variety of pharmacological agents, biological agents and/or drugs, as discussed above and below, may be delivered before, with or after the delivery of a fluid.

Drugs, drug formulations or compositions suitable for administration to a patient may include a pharmaceutically acceptable carrier or solution in an appropriate dosage. There are a number of pharmaceutically acceptable carriers that may be used for delivery of various drugs, for example, via direct injection, oral delivery, suppository delivery, transdermal delivery, epicardial delivery and/or inhalation delivery. Pharmaceutically acceptable carriers include a number of solutions, preferably sterile, for example, water, saline, Ringer's solution and/or sugar solutions such as dextrose in water or saline. Other possible carriers that may be used include sodium citrate, citric acid, amino acids, lactate, mannitol, maltose, glycerol, sucrose, ammonium chloride, sodium chloride, potassium chloride, calcium chloride, sodium lactate, and/or sodium bicarbonate. Carrier solutions may or may not be buffered.

Drug formulations or compositions may include antioxidants or preservatives such as ascorbic acid. They may also be in a pharmaceutically acceptable form for parenteral administration, for example to the cardiovascular system, or directly to the heart, such as intracoronary infusion or injection. Drug formulations or compositions may comprise agents that provide a synergistic effect when administered together. A synergistic effect between two or more drugs or agents may reduce the amount that normally is required for therapeutic delivery of an individual drug or agent. Two or more drugs may be administered, for example, sequentially or simultaneously. Drugs may be administered via one or more bolus injections and/or infusions or combinations thereof. The injections and/or infusions may be continuous or intermittent. Drugs may be administered, for example, systemically or locally, for example, to the heart, to a coronary artery and/or vein, to a pulmonary artery and/or vein, to the right atrium and/or ventricle, to the left atrium and/or ventricle, to the aorta, to the AV node, to the SA node, to a nerve and/or to the coronary sinus. Drugs may be administered or delivered via intravenous, intracoronary and/or intraventricular administration in a suitable carrier. Examples of arteries that may be used to deliver drugs to the AV node include the AV node artery, the right coronary artery, the right descending coronary artery, the left coronary artery, the left anterior descending coronary artery and Kugel's artery. Drugs may be delivered systemically, for example, via oral, transdermal, intranasal, suppository or inhalation methods. Drugs also may be delivered via a pill, a spray, a cream, an ointment or a medicament formulation.

In one embodiment of the present invention, system 900 may include a drug delivery device (not shown). The drug delivery device may comprise a catheter, such as a drug delivery catheter or a guide catheter, a patch, such as a transepicardial patch that slowly releases drugs directly into the myocardium, a cannula, a pump and/or a hypodermic needle and syringe assembly. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. Drugs may be delivered via an iontophoretic drug delivery device placed on the heart. In general, the delivery of ionized drugs may be enhanced via a small current applied across two electrodes.

Positive ions may be introduced into the tissues from the positive pole, or negative ions from the negative pole. The use of iontophoresis may markedly facilitate the transport of certain ionized drug molecules. For example, lidocaine hydrochloride may be applied to the heart via a drug patch comprising the drug. A positive electrode could be placed over the patch and current passed. The negative electrode would contact the heart or other body part at some desired distance point to complete the circuit. One or more of the iontophoresis electrodes may also be used as nerve stimulation electrodes or as cardiac stimulation electrodes.

A drug delivery device may be incorporated into tissue-engaging device 200 and/or ablation device 12, thereby delivering drugs at or adjacent the target tissue site or the drug delivery device may be placed or used at a location differing from the location of tissue-engaging device 200 and/or ablation device 12. For example, a drug delivery device may be placed in contact with the inside surface of a patient's heart while tissue-engaging device 200 and/or ablation device 12 is placed or used on the outside surface of the patient's heart.

The drug delivery device may be slaved to ablation system 10, tissue-engaging device 200, suction source 300, fluid source 400, sensor 60 and/or imaging device 800. For example, a drug delivery device may be designed to automatically stop or start the delivery of drugs during tissue engagement of tissue-engaging device 200 and/or during tissue ablation via ablation device 12. The drug delivery device may be slaved to a robotic system or a robotic system may be slaved to the drug delivery device.

The drug delivery device may comprise one or more switches, e.g., a surgeon-controlled switch. One or more switches may be incorporated in or on the drug delivery device or any other location easily and quickly accessed by the surgeon for regulation of drug delivery by the surgeon. A switch may be, for example, a hand switch, a foot switch, or a voice-activated switch comprising voice-recognition technologies. A switch may be physically wired to the drug delivery device or it may be a remote control switch. The drug delivery device and/or system 900 may include a visual and/or audible signal used to alert a surgeon to any change in the medical procedure, e.g., in the delivery of drugs. For example, a beeping tone or flashing light that increases in frequency as the rate of drug delivery increases may be used to alert the surgeon.

The two divisions of the autonomic nervous system that regulate the heart have opposite functions. First, the adrenergic or sympathetic nervous system increases heart rate by releasing epinephrine and norepinephrine. Second, the parasympathetic system also known as the cholinergic nervous system or the vagal nervous system decreases heart rate by releasing acetylcholine. Catecholamines such as norepinephrine (also called noradrenaline) and epinephrine (also called adrenaline) are agonists for beta-adrenergic receptors. An agonist is a stimulant biomolecule or agent that binds to a receptor.

Beta-adrenergic receptor blocking agents compete with beta-adrenergic receptor stimulating agents for available beta-receptor sites. When access to beta-receptor sites are blocked by receptor blocking agents, also known as beta-adrenergic blockade, the chronotropic or heart rate, inotropic or contractility, and vasodilator responses to receptor stimulating agents are decreased proportionately. Therefore, beta-adrenergic receptor blocking agents are agents that are capable of blocking beta-adrenergic receptor sites.

Since beta-adrenergic receptors are concerned with contractility and heart rate, stimulation of beta-adrenergic receptors, in general, increases heart rate, the contractility of the heart and the rate of conduction of electrical impulses through the AV node and the conduction system.

Drugs, drug formulations and/or drug compositions that may be used according to this invention may include any naturally occurring or chemically synthesized (synthetic analogues) beta-adrenergic receptor blocking agents. Beta-adrenergic receptor blocking agents or β-adrenergic blocking agents are also known as beta-blockers or β-blockers and as class II antiarrhythmics.

The term "beta-blocker" appearing herein may refer to one or more agents that antagonize the effects of beta-stimulating catecholamines by blocking the catecholamines from binding to the beta-receptors. Examples of beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

The effects of administered beta-blockers may be reversed by administration of beta-receptor agonists, e.g., dobutamine or isoproterenol.

The parasympathetic or cholinergic system participates in control of heart rate via the sinoatrial (SA) node, where it reduces heart rate. Other cholinergic effects include inhibition of the AV node and an inhibitory effect on contractile force. The cholinergic system acts through the vagal nerve to release acetylcholine, which, in turn, stimulates cholinergic receptors. Cholinergic receptors are also known as muscarinic receptors. Stimulation of the cholinergic receptors decreases the formation of cAMP. Stimulation of cholinergic receptors generally has an opposite effect on heart rate compared to stimulation of beta-adrenergic receptors. For example, beta-adrenergic stimulation increases heart rate, whereas cholinergic stimulation decreases it. When vagal tone is high and adrenergic tone is low, there is a marked slowing of the heart (sinus bradycardia). Acetylcholine effectively reduces the amplitude, rate of increase and duration of the SA node action potential. During vagal nerve stimulation, the SA node does not arrest. Rather, pacemaker function may shift to cells that fire at a slower rate. In addition, acetylcholine may help open certain potassium channels thereby creating an outward flow of potassium ions and hyperpolarization. Acetylcholine also slows conduction through the AV node.

Drugs, drug formulations and/or drug compositions that may be used according to this invention may include any naturally occurring or chemically synthesized (synthetic analogues) cholinergic agent. The term "cholinergic agent" appearing herein may refer to one or more cholinergic receptor modulators or agonists. Examples of cholinergic agents include, but are not limited to, acetylcholine, carbachol (carbamyl choline chloride), bethanechol, methacholine, arecoline, norarecoline and combinations, mixtures and/or salts thereof.

Drugs, drug formulations and/or drug compositions that may be used according to this invention may include any naturally occurring or chemically synthesized cholinesterase inhibitor. The term "cholinesterase inhibitor" appearing herein may refer to one or more agents that prolong the action of acetylcholine by inhibiting its destruction or hydrolysis by cholinesterase. Cholinesterase inhibitors are also known as acetylcholinesterase inhibitors. Examples of cholinesterase inhibitors include, but are not limited to, edrophonium, neostigmine, neostigmine methylsulfate, pyridostigmine, tacrine and combinations, mixtures and/or salts thereof.

There are ion-selective channels within certain cell membranes. These ion selective channels include calcium channels, sodium channels and/or potassium channels. Therefore, other drugs, drug formulations and/or drug compositions that may be used according to this invention may include any naturally occurring or chemically synthesized calcium channel blocker. Calcium channel blockers inhibit the inward flux of calcium ions across cell membranes of arterial smooth muscle cells and myocardial cells. Therefore, the term "calcium channel blocker" appearing herein may refer to one or more agents that inhibit or block the flow of calcium ions across a cell membrane. The calcium channel is generally concerned with the triggering of the contractile cycle. Calcium channel blockers are also known as calcium ion influx inhibitors, slow channel blockers, calcium ion antagonists, calcium channel antagonist drugs and as class IV antiarrhythmics. A commonly used calcium channel blocker is verapamil.

Administration of a calcium channel blocker, e.g., verapamil, generally prolongs the effective refractory period within the AV node and slows AV conduction in a rate-related manner, since the electrical activity through the AV node depends significantly upon the influx of calcium ions through the slow channel. A calcium channel blocker has the ability to slow a patient's heart rate, as well as produce AV block. Examples of calcium channel blockers include, but are not limited to, amiloride, amlodipine, bepridil, diltiazem, felodipine, isradipine, mibefradil, nicardipine, nifedipine (dihydropyridines), nickel, nimodinpine, nisoldipine, nitric oxide (NO), norverapamil and verapamil and combinations, mixtures and/or salts thereof. Verapamil and diltiazem are very effective at inhibiting the AV node, whereas drugs of the nifedipine family have a lesser inhibitory effect on the AV node. Nitric oxide (NO) indirectly promotes calcium channel closure. NO may be used to inhibit contraction. NO may also be used to inhibit sympathetic outflow, lessen the release of norepinephrine, cause vasodilation, decrease heart rate and decrease contractility. In the SA node, cholinergic stimulation leads to formation of NO.

Other drugs, drug formulations and/or drug compositions that may be used according to this invention may include any naturally occurring or chemically synthesized sodium channel blocker. Sodium channel blockers are also known as sodium channel inhibitors, sodium channel blocking agents, rapid channel blockers or rapid channel inhibitors. Antiarrhythmic agents that inhibit or block the sodium channel are known as class I antiarrhythmics, examples include, but are not limited to, quinidine and quinidine-like agents, lidocaine and lidocaine-like agents, tetrodotoxin, encainide, flecainide and combinations, mixtures and/or salts thereof. Therefore, the term "sodium channel blocker" appearing herein may refer to one or more agents that inhibit or block the flow of sodium ions across a cell membrane or remove the potential difference across a cell membrane. For example, the sodium channel may also be totally inhibited by increasing the extracellular potassium levels to depolarizing hyperkalemic values, which remove the potential difference across the cell membrane. The result is inhibition of cardiac contraction with cardiac arrest (cardioplegia). The opening of the sodium channel (influx of sodium) is for swift conduction of the electrical impulse throughout the heart.

Other drugs, drug formulations and/or drug compositions that may be used according to this invention may include any naturally occurring or chemically synthesized potassium channel agent. The term "potassium channel agent" appearing herein may refer to one or more agents that impact the flow of potassium ions across the cell membrane. There are two major types of potassium channels. The first type of channel is voltage-gated and the second type is ligand-gated. Acetylcholine-activated potassium channels, which are ligand-gated channels, open in response to vagal stimulation and the release of acetylcholine. Opening of the potassium channel causes hyperpolarization, which decreases the rate at which the activation threshold is reached. Adenosine is one example of a potassium channel opener. Adenosine slows conduction through the AV node. Adenosine, a breakdown product of adenosine triphosphate, inhibits the AV node and atria. In atrial tissue, adenosine causes the shortening of the action potential duration and causes hyperpolarization. In the AV node, adenosine has similar effects and also decreases the action potential amplitude and the rate of increase of the action potential. Adenosine is also a direct vasodilator by its actions on the adenosine receptor on vascular smooth muscle cells. In addition, adenosine acts as a negative neuromodulator, thereby inhibiting release of norepinephrine. Class III antiarrhythmic agents also known as potassium channel inhibitors lengthen the action potential duration and refractoriness by blocking the outward potassium channel to prolong the action potential. Amiodarone and d-sotalol are both examples of class III antiarrhythmic agents.

Potassium is the most common component in cardioplegic solutions. High extracellular potassium levels reduce the membrane resting potential. Opening of the sodium channel, which normally allows rapid sodium influx during the upstroke of the action potential, is therefore inactivated because of a reduction in the membrane resting potential.

Drugs, drug formulations and/or drug compositions that may be used according to this invention may comprise one or more of any naturally occurring or chemically synthesized beta-blocker, cholinergic agent, cholinesterase inhibitor, calcium channel blocker, sodium channel blocker, potassium channel agent, adenosine, adenosine receptor agonist, adenosine deaminase inhibitor, dipyridamole, monoamine oxidase inhibitor, digoxin, digitalis, lignocaine, bradykinin agents, serotoninergic agonist, antiarrythmic agents, cardiac glycosides, local anesthetics and combinations or mixtures thereof. Digitalis and digoxin both inhibit the sodium pump. Digitalis is a natural inotrope derived from plant material, while digoxin is a synthesized inotrope. Dipyridamole inhibits adenosine deaminase, which breaks down adenosine. Drugs, drug formulations and/or drug compositions capable of reversibly suppressing autonomous electrical conduction at the SA and/or AV node, while still allowing the heart to be electrically paced to maintain cardiac output may be used according to this invention.

Beta-adrenergic stimulation or administration of calcium solutions may be used to reverse the effects of a calcium channel blocker such as verapamil. Agents that promote heart rate and/or contraction may be used in the present invention. For example, dopamine, a natural catecholamine, is known to increase contractility. Positive inotropes are agents that specifically increase the force of contraction of the heart. Glucagon, a naturally occurring hormone, is known to increase heart rate and contractility. Glucagon may be used to reverse the effects of a beta-blocker since its effects bypass the beta receptor. Forskolin is known to increase heart rate and contractility. As mentioned earlier, epinephrine and norepinephrine naturally increase heart rate and contractility. Thyroid hormone, phosphodiesterase inhibitors and prostacyclin, a prostaglandin, are also known to increase heart rate and contractility. In addition, methylxanthines are known to prevent adenosine from interacting with its cell receptors.

The drug delivery device may include a vasodilative delivery component and/or a vasoconstrictive delivery component. Both delivery components may be any suitable means for delivering vasodilative and/or vasoconstrictive drugs to a site of a medical procedure. For example, the drug delivery device may be a system for delivering a vasodilative spray and/or a vasoconstrictive spray. The drug delivery device may be a system for delivering a vasodilative cream and/or a vasoconstrictive cream. The drug delivery device may be a system for delivering any vasodilative formulation such as an ointment or medicament etc. and/or any vasoconstrictive formulation such as an ointment or medicament etc. or any combination thereof.

The drug delivery device may comprise a catheter, such as a drug delivery catheter or a guide catheter, for delivering a vasodilative substance followed by a vasoconstrictive substance. A drug delivery catheter may include an expandable member, e.g., a low-pressure balloon, and a shaft having a distal portion, wherein the expandable member is disposed along the distal portion. A catheter for drug delivery may comprise one or more lumens and may be delivered endovascularly via insertion into a blood vessel, e.g., an artery such as a femoral, radial, subclavian or coronary artery. The catheter can be guided into a desired position using various guidance techniques, e.g., flouroscopic guidance and/or a guiding catheter or guide wire techniques. In one embodiment, one catheter may be used to deliver both a vasodilative component and a vasoconstrictive component. The drug delivery device may be a patch, such as a transepicardial patch that slowly releases drugs directly into the myocardium, a cannula, a pump and/or a hypodermic needle and syringe assembly. The drug delivery device may be an iontophoretic drug delivery device placed on the heart.

A vasodilative component may comprise one or more vasodilative drugs in any suitable formulation or combination. Examples of vasodilative drugs include, but are not limited to, a vasodilator, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine and a dopamine D1-like receptor agonist, stimulant or activator. The vasodilative component may include a pharmaceutically acceptable carrier or solution in an appropriate dosage.

A vasoconstrictive component may comprise one or more suitable vasoconstrictive drugs in any suitable formulation or combination. Examples of vasoconstrictive drugs include, but are not limited to, a vasoconstrictor, a sympathomimetic, methoxamine hydrochloride, epinephrine, midodrine hydrochloride, desglymidodrine, and an alpha-receptor agonist, stimulant or activator. The vasoconstrictive component may include a pharmaceutically acceptable carrier or solution in an appropriate dosage Controller 16 may process sensed information from a sensor. The controller may store and/or process such information before, during and/or after a medical procedure, e.g., an ablation procedure. For example, the patient's tissue temperature may be sensed, stored and processed prior to and during the ablation procedure.

Controller 16 may be used to control the energy supplied to one or more energy transfer elements, e.g., electrodes or transducers, of tissue-engaging device 200 and/or ablation device 12. Controller 16 may also gather and process information from one or more sensors. This information may be used to adjust energy levels and times. Controller 16 may incorporate one or more switches to facilitate regulation of the various system components by the surgeon. One example of such a switch is a foot pedal. A switch may also be, for example, a hand switch, or a voice-activated switch compris-ing voice-recognition technologies. A switch may be physically wired to controller 16 or it may be a remote control switch. A switch may be incorporated in or on one of the surgeon's instruments, such as surgical site retractor, e.g., a sternal or rib retractor, tissue-engaging device 200 and/or ablation device 12, or any other location easily and quickly accessed by the surgeon. Controller 16 may also include a display. Controller 16 may also include other means of indicating the status of various components to the surgeon such as a numerical display, gauges, a monitor display or audio feedback.

Controller 16 may incorporate a cardiac stimulator and/or cardiac monitor. For example, electrodes used to stimulate or monitor the heart may be incorporated into tissue-engaging device 200 and/or ablation device 12. Controller 16 may incorporate a nerve stimulator and/or nerve monitor. For example, electrodes used to stimulate or monitor one or more nerves, e.g., a vagal nerve, may be incorporated into tissue-engaging device 200 and/or ablation device 12. Controller 16 may comprise a surgeon-controlled switch for cardiac stimulation and/or monitoring, as discussed earlier. Controller 16 may comprise a surgeon-controlled switch for nerve stimulation and/or monitoring, as discussed earlier. Cardiac stimulation may comprise cardiac pacing and/or cardiac defibrillation. Controller 16, tissue-engaging device 200 and/or ablation device 12 may incorporate a cardiac mapping device for mapping the electrical signals of the heart.

A visual and/or audible signal used to alert a surgeon to the completion or resumption of energy delivery, suction, sensing, monitoring, stimulation and/or delivery of fluids, drugs and/or cells may be incorporated into controller 16. For example, a beeping tone or flashing light that increases in frequency as the energy delivered increases.

System 900 may include sensor 600. Sensor 600 may be incorporated into tissue-engaging device 200 and/or ablation device 12 or it may be incorporated into another separate device. A separate sensor device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof.

Sensor 600 may comprise one or more switches, e.g., a surgeon-controlled switch. One or more switches may be incorporated in or on a sensor device or any other location easily and quickly accessed by the surgeon for regulation of sensor 600 by the surgeon. A switch may be, for example, a hand switch, a foot switch, or a voice-activated switch comprising voice-recognition technologies. A switch may be physically wired to sensor 600 or it may be a remote control switch.

Sensor 600 may include a visual and/or audible signal used to alert a surgeon to any change in the measured parameter, for example, tissue temperature, cardiac hemodynamics or ischemia. A beeping tone or flashing light may be used to alert the surgeon that a change has occurred in the parameter sensed.

Sensor 600 may comprise one or more temperature-sensitive elements, such as a thermocouple, to allow a surgeon to monitor temperature changes of a patient's tissue. Alternatively, sensor 600 may sense and/or monitor voltage, amperage, wattage and/or impedance. For example, an ECG sensor may allow a surgeon to monitor the hemodynamics of a patient during a heart positioning procedure. The heart may become hemodynamically compromised during positioning and while in a non-physiological position. Alternatively, sensor 600 may be any suitable blood gas sensor for measuring the concentration or saturation of a gas in the blood or tissues. For example, sensor 600 may be a sensor for measuring the concentration or saturation of oxygen or carbon dioxide in the blood or tissues. Alternatively, sensor 600 may be any suitable sensor for measuring blood pressure or flow, for example a Doppler ultrasound sensor system, or a sensor for measuring hematocrit (HCT) levels.

Alternatively sensor 600 may be a biosensor, for example, comprising an immobilized biocatalyst, enzyme, immunoglobulin, bacterial, mammalian or plant tissue, cell and/or subcellular fraction of a cell. For example, the tip of a biosensor may comprise a mitochondrial fraction of a cell, thereby providing the sensor with a specific biocatalytic activity.

Sensor 600 may be based on potentiometric technology or fiber optic technology. For example, the sensor may comprise a potentiometric or fiber optic transducer. An optical sensor may be based on either an absorbance or fluorescence measurement and may include an UV, a visible or an IR light source.

Sensor 600 may be used to detect naturally detectable properties representative of one or more characteristics, e.g., chemical, physical, mechanical, thermal, electrical or physiological, of system 900 and/or a patient's bodily tissues or fluids. For example, naturally detectable properties of patient's bodily tissues or fluids may include pH, fluid flow, electrical current, impedance, temperature, pressure, tension, components of metabolic processes, chemical concentrations, for example, the absence or presence of specific peptides, proteins, enzymes, gases, ions, etc. Naturally detectable properties of system 900 may include, for example, pressure, tension, stretch, fluid flow, electrical, mechanical, chemical and/or thermal. For example, sensor 600 may be used to sense, monitor and/or control suction or vacuum delivered from suction source 300. Sensor 600 may be used to measure suction between device 200 and tissue. Sensor 600 may be used to sense, monitor and/or control fluid delivered from fluid source 400. Sensor 600 may be used to sense, monitor and/or control energy delivered from power supply 14 via controller 16.

Sensor 600 may include one or more imaging systems, camera systems operating in UV, visible, or IR range; electrical sensors; voltage sensors; current sensors; piezoelectric sensors; electromagnetic interference (EMI) sensors; photographic plates, polymer-metal sensors; charge-coupled devices (CCDs); photo diode arrays; chemical sensors, electrochemical sensors; pressure sensors, vibration sensors, sound wave sensors; magnetic sensors; UV light sensors; -visible light sensors; IR light sensors; radiation sensors; flow sensors; temperature sensors; or any other appropriate or suitable sensor.

Sensor 600 may be incorporated into tissue-engaging device 200 and/or ablation device 12 or sensor 600 may be placed or used at a location differing from the location of tissue-engaging device 200 and/or ablation device 12. For example, sensor 600 may be placed in contact with the inside surface of a patient's heart while tissue-engaging device 200 and/or ablation device 12 is placed or used on the outside surface of the patient's heart.

Ablation assembly 10, tissue-engaging device 200, suction source 300, fluid source 400, drug delivery device and/or processor 800 may be slaved to sensor 600. For example, tissue-engaging device 200 may be designed to automatically adjust suction if sensor 600 measures a predetermined sensor value, e.g., a particular suction value, or ablation device 12 may be designed to stop or start the ablation of tissue if sensor 600 measures a predetermined sensor value, e.g., a particular tissue temperature.

Sensor 600 may include a visual and/or audible signal used to alert a surgeon to any change in the one or more characteristics the sensor is sensing and/or monitoring. For example, a beeping tone or flashing light that increases in frequency as tissue temperature rises may be used to alert the surgeon.

Controller 16 may include one or more processors. A processor may receive and preferably interpret the signal from sensor 600. A processor may comprise software and/or hardware. A processor may comprise fuzzy logic. A suitable amplifier may amplify signals from sensor 600 before reaching a processor. The amplifier may be incorporated into a processor. Alternatively the amplifier may be incorporated into sensor 600 or tissue-engaging device 200 or ablation device 12. Alternatively, the amplifier may be a separate device. A processor may be a device separate from ablation assembly 10, tissue-engaging device 200, suction source 300, fluid source 400, sensor 600 and/or imaging device 800. A processor may be incorporated into ablation device 12, tissue-engaging device 200, suction source 300, fluid source 400, sensor 600 and/or imaging device 800. A processor may control the energy delivered from the power supply 14. For example, a signal of a first intensity from sensor 600 may indicate that the energy level from power supply 14 should be lowered; a signal of a different intensity may indicate that power supply 14 should be turned off. Preferably, a processor may be configured so that it may automatically raise or lower the suction delivered to device 12 and/or device 200 from suction source 300, the fluids delivered to device 12 and/or device 200 from fluid source 400 and/or the energy delivered to device 12 and/or device 200 from power supply 14. Alternatively, the control of suction source 300, fluid source 400 and/or power supply 14 based on output from a processor may be manual.

Controller 16 may include a visual display or monitor, such as, for example, a LCD or CRT monitor, to display various amounts and types of information. By software control, the user may choose to display the information in a number of ways. The monitor may show, for example, a currently sensed parameter, e.g., temperature. The monitor may also lock and display the maximum sensed value achieved. Sensed information may be displayed to the user in any suitable manner, such as for example, displaying a virtual representation of ablation device 12 and/or tissue-engaging device 200 on the monitor.

Alternatively, the monitor may display the voltage corresponding to the signal emitted from sensor 600. This signal corresponds in turn to the intensity of a sensed parameter at the target tissue site. Therefore a voltage level of 2 would indicate that the tissue was, for example, hotter than when the voltage level was 1. In this example, a user would monitor the voltage level and, if it exceeded a certain value, would turn off or adjust the power supply 14.

The display of controller 16 may alternatively be located on ablation device 12, power supply 14, tissue-engaging device 200, suction source 300, fluid source 400, sensor 600 and/or imaging device 800. An indicator, such as an LED light, may be permanently or removeably incorporated into ablation device 12, power supply 14, tissue-engaging device 200, suction source 300, fluid source 400, sensor 600 and/or imaging device 800. The indicator may receive a signal from sensor 600 indicating that the tissue had reached an appropriate value, for example temperature. In response, the indicator may turn on, change color, grow brighter or change in any suitable manner to indicate that the flow of energy from power supply 14 should be modified or halted. The indicator may also be located on ablation device 12, power supply 14, tissue-engaging device 200, suction source 300, fluid source 400, sensor 60 and/or imaging device 800 and/or may be located on another location visible to the user.

Controller 16 may include an audio device that indicates to the user that the delivery of suction, fluids and/or energy should be halted or adjusted. Such an audio device may be, for example, a speaker that broadcasts a sound (for example, a beep) that increases in intensity, frequency or tone as a parameter sensed by sensor 600 increases. The user may adjust, for example, turn down or turn off power supply 14 when the sound emitted reaches a given volume or level. In another embodiment, the audio device may also give an audible signal (such as the message "turn off energy source"), for example, when a parameter sensed by sensor 600 reaches a certain level. Such an audio device may be located on tissue-engaging device 200, suction source 300, fluid source 400, sensor 600 and/or imaging device 800. The audio device may also be a separate device.

In one embodiment of the present invention, system 900 may include an imaging device 900. Imaging device 900 may be based on one or more imaging modalities such as ultrasound imaging, CT, MRI, PET, fluoroscopy, echocardiography, etc. The coordinates for the desired area of ablation, for example, from any of these imaging modalities can be electronically fed to controller 16 such that the desired ablation pattern can be generated and ablated. The imaging device may have two and/or three-dimensional imaging capabilities as well as phased and/or annular array imaging capabilities. For example, two or three-dimensional echocardiography, such as transesophageal echocardiography (TEE), or ultrasound imaging, such as transthoracic ultrasound imaging may be possible with use of imaging device 900.

The imaging device may comprise one or more light sources and/or illuminating materials, e.g., glow-in-the-dark materials. For example, the tissue-engaging head of device 200 and/or one or more portions of ablation device 12 may comprise one or more glow-in-the-dark materials. The imaging device may be based on fluorescence technologies. The imaging device may comprise fiber optic technologies; for example a fiber optic conduit may deliver light from a remote light source to an area adjacent tissue-engaging device 200 and/or ablation device 12 for illumination of a treatment site.

The imaging device may comprise a light pipe, for example, to illuminate the tissue-engaging head of device 200 and/or ablation device 12 and/or the surgical field adjacent device 200 and/or device 12. A transparent, semi-transparent or translucent tissue-engaging head may be illuminated merely by placement of the end of a light pipe or other light source adjacent the tissue-engaging head of device 200. A transparent, semi-transparent or translucent portion of ablation device 12 may be illuminated merely by placement of the end of a light pipe or other light source adjacent the transparent, semi-transparent or translucent portion of ablation device 12.

The imaging device may include a visual display or monitor, such as, for example, a LCD or CRT monitor, to display various amounts and types of information. By software control, the user may choose to display the information in a number of ways. The imaging device may be powered by AC current, DC current, or it may be battery powered either by a disposable or re-chargeable battery. The imaging device may provide UV, IR and/or visible light. The imaging device may include a laser. The imaging device may be incorporated into tissue-engaging device 200 and/or ablation device 12 or it may be incorporated into a separate device. A separate imaging device may be positioned and used, for example, through a thoracotomy, through a sternotomy, percutaneously, transvenously, arthroscopically, endoscopically, for example, through a percutaneous port, through a stab wound or puncture, through a small incision, for example, in the chest, in the groin, in the abdomen, in the neck or in the knee, or in combinations thereof. A separate imaging device may be positioned through one or more body cavity openings of the patient and/or positioned outside the patient, e.g., on the skin of the patient. One or more imaging devices may be positioned in the esophagus, the trachea and/or the bronchi of the lungs.

The imaging device may comprise one or more switches, e.g., a surgeon-controlled switch. One or more switches may be incorporated in or on the imaging device or any other location easily and quickly accessed by the surgeon for regulation of the imaging device by the surgeon. A switch may be, for example, a hand switch, a foot switch, or a voice-activated switch comprising voice-recognition technologies. A switch may be physically wired to the imaging device or it may be a remote control switch.

Ablation assembly 10, tissue-engaging device 200, suction source 300, fluid source 400, a drug delivery device and/or imaging device may be slaved to a robotic system or a robotic system may be slaved to ablation assembly 10, tissue-engaging device 200, suction source 300, fluid source 400, sensor 60, a drug delivery device and/or imaging device. Computer- and voice-controlled robotic systems that position and maneuver endoscopes and/or other surgical instruments for performing microsurgical procedures through small incisions may be used by the surgeon to perform precise and delicate maneuvers. These robotic systems may allow the surgeon to perform a variety of microsurgical procedures. In general, robotic systems may include head-mounted displays which integrate 3-D visualization of surgical anatomy and related diagnostic and monitoring data, miniature high resolution 2-D and 3-D digital cameras, a computer, a high power light source and a standard video monitor.

A medical procedure wherein one or more components of system 900 may be used may be non-invasive, minimally invasive and/or invasive. The medical procedure may entail a port-access approach, a partially or totally endoscopic approach, a sternotomy approach or a thoracotomy approach. The medical procedure may include the use of various robotic or imaging systems. The medical procedure may be surgery on the heart. Alternatively, the medical procedure may be surgery performed on another organ of the body.

In one embodiment of the present invention, a positioning or tissue-engaging device may comprise one or more sensors and/or electrodes, e.g., sensing electrodes and/or stimulation electrodes. In another embodiment of the present invention, an imaging device may comprise one or more sensors and/or electrodes, e.g., sensing electrodes and/or stimulation electrodes. In another embodiment of the present invention, a positioning or tissue-engaging device may comprise imaging capabilities, e.g., ultrasound imaging, and one or more sensors and/or electrodes, e.g., sensing electrodes and/or stimulation electrodes.

In one embodiment of the present invention, an ablation device may comprise one or more sensors and/or electrodes, e.g., sensing electrodes and/or stimulation electrodes. In another embodiment of the present invention, an ablation device may comprise imaging capabilities, e.g., ultrasound imaging, and/or one or more electrodes, e.g., stimulation electrodes. In another embodiment of the present invention, an ablation device may comprise tissue-positioning capabilities, e.g., suction engagement of tissue. In one embodiment of the invention, ablation device 12 may be guided or steerable.

Figure 18B:
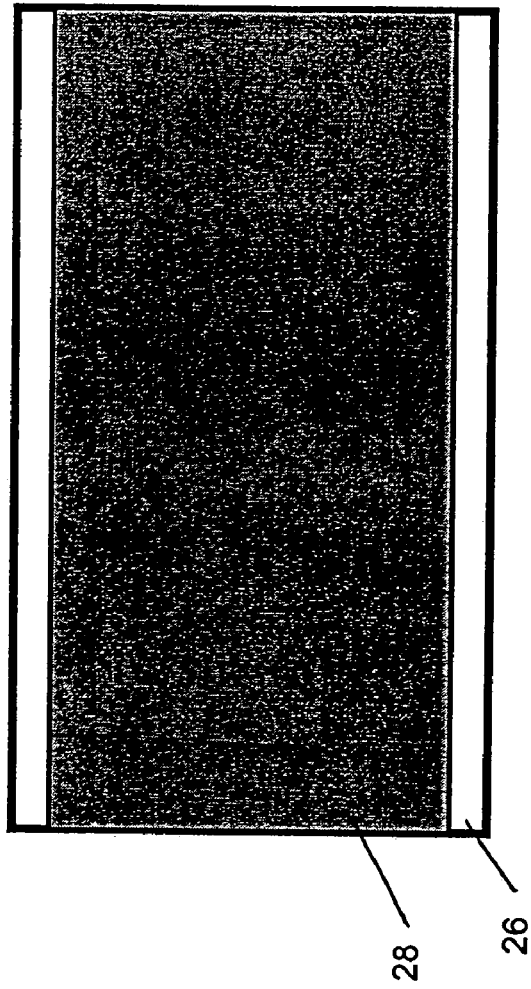
FIG. 18b is a bottom view of a portion of an ultrasound emitting member of a focused ultrasound ablation device of the high intensity focused ultrasound stimulation or ablation assembly.
Figure 18C:
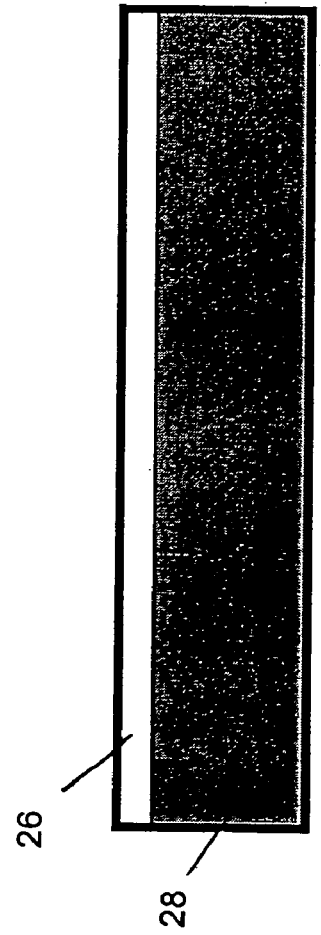
FIG. 18c is a side view of a portion of an ultrasound emitting member of a focused ultrasound ablation device of the high intensity focused ultrasound stimulation or ablation assembly.
Figure 18A:
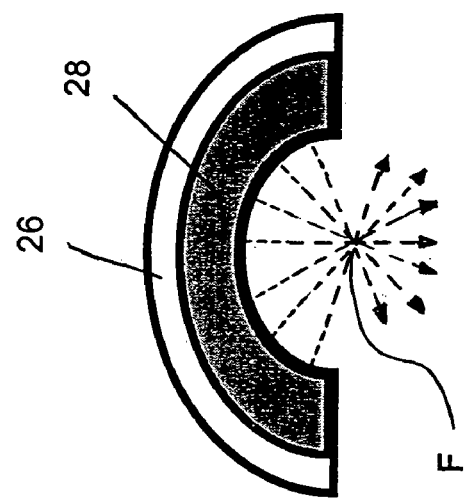
FIG. 18a is a cross-sectional view of a portion of an ultrasound emitting member of a focused ultrasound ablation device of the high intensity focused ultrasound stimulation or ablation assembly.
Figure 19:
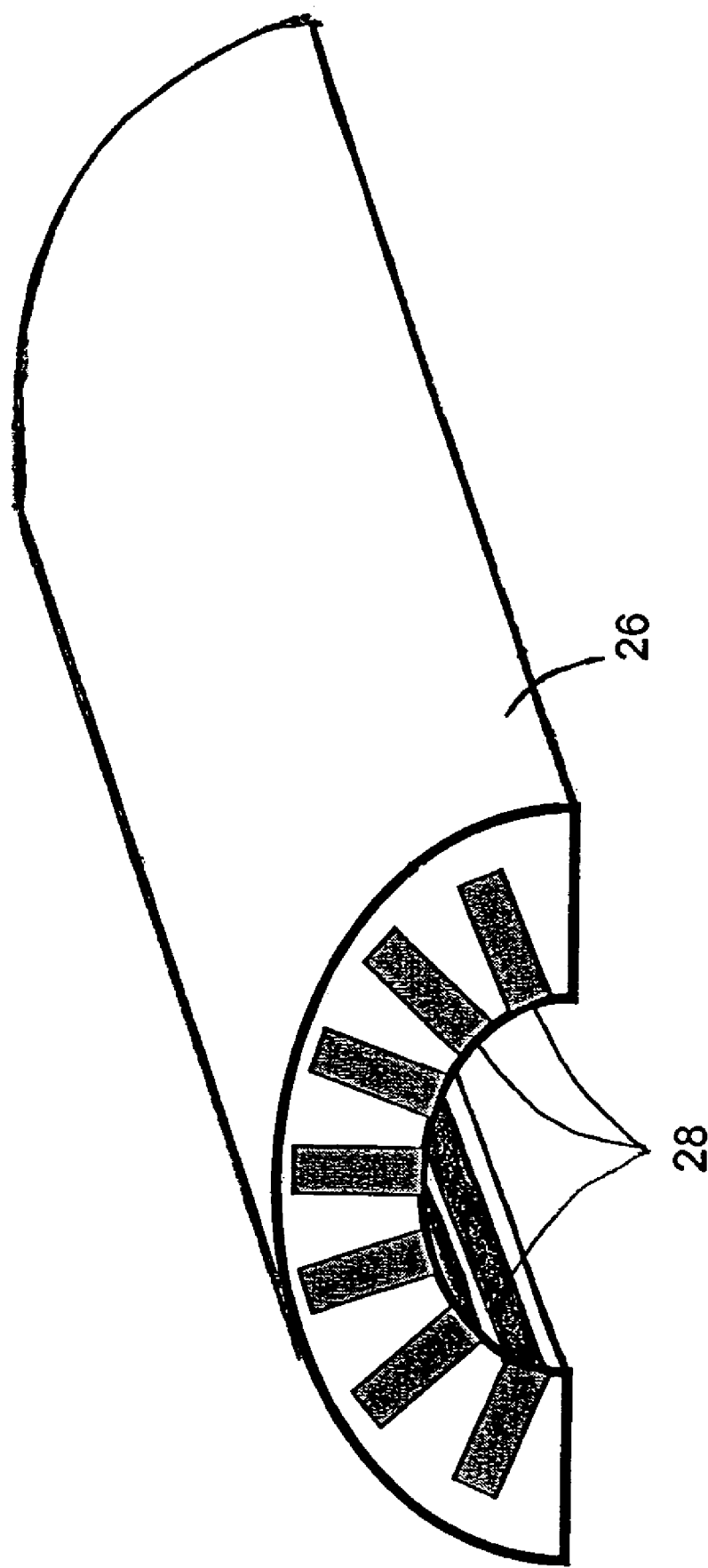
FIG. 19 is a cross-sectional view of a portion of an ultrasound emitting member of a focused ultrasound ablation device of the high intensity focused ultrasound stimulation or ablation assembly.

In one embodiment of the present invention, transducer elements 28 may comprise one or more configurations varying in size and shape. For example, transducer elements 28 may be round, as shown in FIG. 2. Alternatively, transducer elements 28 may be elongated or linear in shape, as shown in FIGS. 18 and 19. Transducers elements 28 may be arranged on or in housing 26 in various configurations. In FIG. 2, for example, transducers elements 28 are shown arranged in a planar array of three rows R and six columns C, although the transducer elements can be arranged in any number of rows and columns. Alternatively, the transducer elements may be angled to a more central area to create a lesion of a desired shape rather than in a row aimed along the same axis. In FIG. 19, elongated transducer elements 28 are shown arranged along a curve. Housing 26 may be configured to have one or more shapes, such as a round shape, an oval shape, a square shape, a rectangular shape, a triangular shape, a concave cave shape, a convex shape, a flat shape, etc. In FIG. 2, for example, housing 26 is shown to have a flat, rectangular shape. Alternatively, in FIGS. 18 and 19, for example, housing 26 is shown to have a concave, rectangular shape. The transducer elements 28, in FIG. 19, are shown aligned relatively parallel to each other. Linear transducer elements as shown in FIGS. 18 and 19 would be capable of producing a line of focused energy.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference in its entirety, as if each such patent or publication were individually incorporated by reference herein.

We claim:

1. A method of performing an ultrasound ablation procedure on a heart of a patient, comprising:
   providing a tissue-engaging device;
   engaging the heart with the tissue-engaging device;
   positioning the heart into a non-physiological orientation;
   adjusting the beating of the heart;
   positioning a portion of an ultrasound ablation device through a mouth of the patient; and
   performing an ultrasound ablation procedure on the heart.

2. The method of claim 1 wherein the step of adjusting the beating of the heart temporarily slows the beating of the heart.

3. The method of claim 1 wherein the step of adjusting the beating of the heart temporarily stops the beating of the heart.

4. The method of claim 1 wherein the step of adjusting the beating of the heart includes stimulating a nerve.

5. The method of claim 4 further comprising reducing or stopping stimulation of the nerve to allow the heart to beat naturally.

6. The method of claim 4 further comprising the step of stimulating the nerve a subsequent time in order to re-adjust the beating of the heart.

7. The method of claim 4 further comprising the step of stimulating the heart via a pacing device following the completion of stimulating the nerve.

8. The method of claim 4 wherein the nerve is a vagal nerve.

9. The method of claim 4 wherein the nerve is stimulated using an endotracheal, an endoesophageal, an intravascular, a transcutaneous, or an intracutaneous stimulation technique.

10. The method of claim 1 further comprising the step of administering at least one drug during the ablation procedure.

11. The method of claim 10 wherein the drug adjusts the beating of the heart.

12. The method of claim 10 wherein the drug is selected from the group consisting of: a beta-blocker, a cholinergic agent, a cholinesterase inhibitor, a calcium channel blocker, a sodium channel blocker, a potassium channel agent, adenosine, an adenosine receptor agonist, an adenosine deaminase inhibitor, dipyridamole, a monoamine oxidase inhibitor, digoxin, digitalis, lignocaine, a bradykinin agent, a serotoninergic agonist, an antiarrythmic agent, a cardiac glycoside, a local anesthetic, atropine, a calcium solution, an agent that promotes heart rate, an agent that promotes heart contractions, dopamine, a catecholamine, an inotrope glucagon, a hormone, forskolin, epinephrine, norepinephrine, thyroid hormone, a phosphodiesterase inhibitor, prostacyclin, prostaglandin and a methylxanthine.

13. The method of claim 1 further comprising the step of positioning the heart a subsequent time into a different non-physiological orientation.

14. The method of claim 1 further comprising the step of delivering one or more fluids during the ablation procedure.

15. The method of claim 14 wherein the one or more fluids comprises at least one diagnostic agent, therapeutic agent or biological agent.

16. The method of claim 1 wherein a portion of the ultrasound ablation device is positioned within a trachea of the patient.

17. The method of claim 1 wherein a portion of the ultrasound ablation device is positioned within a bronchi of the patient.

18. The method of claim 1 wherein a portion of the ultrasound ablation device is positioned within an esophagus of the patient.

19. A system of ablating a heart of a patient comprising:
   a tissue engaging device configured to engage the heart and position the heart in a desired orientation to a desired location in a body cavity of the a patient;
   a stimulator configured to deliver stimulating energy to the heart, altering a heart rate of the heart upon receipt of the stimulating energy;
   an ablation device configured to generate the ablation energy a predetermined distance from ablation device, configured to be introduced to the location of the body cavity through a mouth of the patient and configured to focus the ablation energy at the predetermined distance to adequately deliver the ablation energy from the location in the body cavity to the heart; and
   a controller, operatively coupled to the ablation device and to the stimulator, the controller being configured to synchronize delivery of the stimulating energy to the heart via the stimulator and the ablation energy to the heart via the ablation device.

20. The system of claim 19 wherein a distal end of the ablation device is sized and shaped to be positioned within the body cavity connected to the mouth of the patient.

21. The system of claim 20 wherein the body cavity is an esophagus cavity.

22. The system of claim 20 wherein the body cavity is a thoracic cavity.

23. The system of claim 20 wherein the body cavity is a trachea or bronchi cavity.

24. The system of claim 19 wherein the tissue-engaging device is a suction device.

25. The system of claim 19 wherein the stimulator is a nerve stimulation device.

26. The system of claim 19 wherein the stimulator is a drug delivery device.

* * * * *